US006432127B1

(12) United States Patent
Kim et al.

(10) Patent No.: US 6,432,127 B1
(45) Date of Patent: Aug. 13, 2002

(54) DEVICES FOR FORMING AND/OR MAINTAINING CONNECTIONS BETWEEN ADJACENT ANATOMICAL CONDUITS

(75) Inventors: Steven Kim, San Jose; J. Christopher Flaherty, Los Altos; Jason Brian Whitt, San Francisco; Theodore C. Lamson, Pleasanton; Joshua Makower, Los Altos, all of CA (US)

(73) Assignee: TransVascular, Inc., Menlo Park, CA (US)

( * ) Notice: Subject to any disclaimer, the term of this patent is extended or adjusted under 35 U.S.C. 154(b) by 0 days.

(21) Appl. No.: 08/970,694

(22) Filed: Nov. 14, 1997

Related U.S. Application Data

(63) Continuation-in-part of application No. PCT/US97/01468, filed on Jan. 31, 1997, and a continuation-in-part of application No. 08/730,327, filed on Oct. 11, 1996, and a continuation-in-part of application No. 08/730,496, filed on Oct. 11, 1996, now Pat. No. 5,830,222.

(51) Int. Cl.[7] .............................. A61F 2/06; A61M 5/00
(52) U.S. Cl. ...................................... 623/1.11; 606/198
(58) Field of Search ................................ 606/191, 192, 606/193, 194, 195, 198, 200, 152, 153, 154, 155, 156; 623/1.11, 1.12, 1.13, 1.15, 1.16, 1.22, 1.23; 604/96, 104

(56) References Cited

U.S. PATENT DOCUMENTS

| 4,580,568 A | 4/1986 | Gianturco | 128/345 |
|---|---|---|---|
| 4,800,882 A | 1/1989 | Gianturco | 128/343 |
| 4,856,516 A | 8/1989 | Hillstead | 128/343 |
| 5,035,706 A | 7/1991 | Giantureo et al. | 606/198 |
| 5,282,824 A | 2/1994 | Gianturco | 606/198 |
| 5,292,331 A | 3/1994 | Boneau | 606/198 |
| 5,314,472 A | 5/1994 | Fontaine | 623/12 |

(List continued on next page.)

FOREIGN PATENT DOCUMENTS

| DE | 29702671 | 5/1997 | ............ A61F/2/04 |
|---|---|---|---|
| EP | 647438 | 4/1995 | ............ A61F/2/06 |
| EP | 707837 | 4/1996 | ............ A61F/2/06 |
| WO | 9424961 | 11/1994 | ............ A61F/2/06 |
| WO | 9612517 | 5/1996 | .......... A61M/29/00 |
| WO | 9613228 | 5/1996 | ............ A61F/2/06 |
| WO | 9619952 | 7/1996 | ............ A61F/2/04 |
| WO | 9749353 | 12/1997 | ............ A61F/2/06 |
| WO | 9800090 | 1/1998 | ............ A61J/2/06 |
| WO | 9807387 | 2/1998 | ............ A61F/2/06 |
| WO | 9807388 | 2/1998 | ............ A61F/2/06 |
| WO | 9807390 | 2/1998 | ............ A61F/2/06 |
| WO | 9809583 | 3/1998 | ............ A61F/2/06 |
| WO | 9812988 | 4/1998 | ............ A61F/2/06 |
| WO | 9817204 | 4/1998 | ............ A61F/2/06 |
| WO | 9819608 | 5/1998 | ........... A61B/17/22 |

(List continued on next page.)

OTHER PUBLICATIONS

Jostent; Coronary Stent Graft, The Best of Both Worlds.
Ulrich Sigwart; An Overview of Intravascular Stents: Old and New; 803–815pp.

Primary Examiner—David J. Isabella
(74) Attorney, Agent, or Firm—Robert D. Buyan; Stout, Uxa, Buyan & Mullins, LLP

(57) ABSTRACT

Implantable connector devices which are useable to maintain fluidic connection between, or approximation of, openings formed in adjacent natural or prosthetic anatomical conduits (or adjacent openings formed in a single anatomical conduits). These connector devices generally comprise a plurality of radially expandable annular members having one or more elongate strut members extending therebetween. Initially, the device is mountable on or within a delivery catheter while in a radially compact configuration. After the delivery catheter has been inserted into the body, the device is caused to transition to a radially expanded configuration whereby it becomes implanted within the body so as to maintain the desired fluidic connection between, or the desired approximation of, the anatomical conduit(s).

125 Claims, 23 Drawing Sheets

U.S. PATENT DOCUMENTS

| | | | |
|---|---|---|---|
| 5,383,892 A | | 1/1995 | Cardon et al. .............. 606/198 |
| 5,449,373 A | | 9/1995 | Pinchasik et al. ........... 606/198 |
| 5,507,767 A | | 4/1996 | Maeda et al. ............... 606/198 |
| 5,527,354 A | | 6/1996 | Fontaine et al. ............... 623/1 |
| 5,540,712 A | | 7/1996 | Kleshinski et al. ......... 606/198 |
| 5,540,713 A | | 7/1996 | Schnepp-Pesch et al. ... 606/198 |
| 5,545,210 A | | 8/1996 | Hess et al. ..................... 623/1 |
| 5,554,181 A | | 9/1996 | Das ................................ 623/1 |
| 5,556,414 A | * | 9/1996 | Turi ............................... 623/1 |
| 5,569,295 A | | 10/1996 | Lam ............................ 606/198 |
| 5,571,135 A | | 11/1996 | Fraser et al. ................. 606/198 |
| 5,571,168 A | | 11/1996 | Toro .............................. 623/1 |
| 5,591,195 A | | 1/1997 | Taheri et al. ............... 606/194 |
| 5,593,442 A | * | 1/1997 | Klein ............................. 623/1 |
| 5,603,698 A | | 2/1997 | Roberts et al. ............. 604/104 |
| 5,603,721 A | | 2/1997 | Lau et al. ................... 606/195 |
| 5,628,786 A | | 5/1997 | Banas et al. ................... 623/1 |
| 5,665,115 A | | 9/1997 | Cragg ............................ 623/1 |
| 5,676,670 A | | 10/1997 | Kim ............................ 606/108 |
| 5,683,411 A | | 11/1997 | Kavteladze et al. ........ 606/200 |
| 5,695,516 A | | 12/1997 | Fischell et al. ............. 606/194 |
| 5,697,948 A | | 12/1997 | Marin et al. ................ 606/198 |
| 5,697,971 A | | 12/1997 | Fischell et al. ................ 623/1 |
| 5,702,418 A | | 12/1997 | Ravenscroft ................ 606/198 |
| 5,702,419 A | | 12/1997 | Berry et al. ................. 606/198 |
| 5,707,386 A | | 1/1998 | Schnepp-Pesch et al. ... 606/194 |
| 5,713,917 A | | 2/1998 | Leonhardt et al. .......... 606/194 |
| 5,713,949 A | | 2/1998 | Jayaraman ..................... 623/1 |
| 5,716,393 A | | 2/1998 | Lindenberg et al. ........... 623/1 |
| 5,725,548 A | | 3/1998 | Jayaraman .................. 606/198 |
| 5,725,572 A | | 3/1998 | Lam et al. ...................... 623/1 |
| 5,728,131 A | | 3/1998 | Frantzen et al. ............ 606/194 |
| 5,733,267 A | | 3/1998 | Del Toro .................... 604/280 |
| 5,735,893 A | | 4/1998 | Lau et al. ....................... 623/1 |
| 5,741,327 A | | 4/1998 | Frantzen ........................ 623/1 |
| 5,741,333 A | | 4/1998 | Frid ............................. 623/12 |
| 5,746,766 A | | 5/1998 | Edoga ......................... 606/198 |
| 5,752,961 A | | 5/1998 | Hill ............................. 606/113 |
| 5,755,769 A | | 5/1998 | Richard et al. .............. 623/11 |
| 5,755,771 A | | 5/1998 | Penn et al. ..................... 623/1 |
| 5,755,773 A | | 5/1998 | Evans et al. ................... 623/1 |
| 5,755,775 A | | 5/1998 | Trerotola et al. .............. 623/1 |
| 5,759,192 A | | 6/1998 | Saunders .................... 606/194 |
| 5,766,238 A | * | 6/1998 | Lau et al. ....................... 623/1 |
| 5,766,239 A | | 6/1998 | Cox ............................... 623/1 |
| 5,772,669 A | | 6/1998 | Vrba ........................... 606/108 |
| 5,776,140 A | | 7/1998 | Cottone ...................... 606/108 |
| 5,776,161 A | | 7/1998 | Globerman .................. 606/194 |
| 5,776,181 A | | 7/1998 | Lee et al. ....................... 623/1 |
| 5,776,183 A | | 7/1998 | Kanesaka et al. .............. 623/1 |
| 5,779,731 A | | 7/1998 | Leavitt ........................ 606/194 |
| 5,782,855 A | | 7/1998 | Lau et al. .................... 606/194 |
| 5,782,906 A | * | 7/1998 | Marshall et al. ............... 623/1 |
| 5,792,144 A | | 8/1998 | Fischell et al. ............. 606/108 |
| 5,797,920 A | | 8/1998 | Kim ............................ 606/108 |
| 5,800,517 A | | 9/1998 | Anderson et al. .............. 623/1 |
| 5,800,522 A | | 9/1998 | Campbell et al. .............. 623/1 |
| 5,810,837 A | | 9/1998 | Hofmann et al. ........... 606/108 |
| 5,810,872 A | | 9/1998 | Kanesaka et al. ........... 606/198 |
| 5,814,063 A | | 9/1998 | Freitag ........................ 606/198 |
| 5,817,126 A | | 10/1998 | Imran .......................... 606/198 |
| 5,824,061 A | | 10/1998 | Quijano et al. ................. 623/2 |
| 5,827,321 A | | 10/1998 | Roubin et al. .............. 606/195 |
| 5,836,965 A | | 11/1998 | Jendersee et al. ........... 606/198 |
| 5,836,966 A | | 11/1998 | St. Germain ................ 606/198 |
| 5,851,228 A | * | 12/1998 | Pinheiro ......................... 623/1 |
| 5,868,780 A | | 2/1999 | Lashinski et al. ........... 606/198 |
| 5,868,783 A | * | 2/1999 | Tower ............................ 623/1 |

FOREIGN PATENT DOCUMENTS

| | | | |
|---|---|---|---|
| WO | 9819629 | 5/1998 | ............ A61F/2/06 |
| WO | 9819630 | 5/1998 | ............ A61F/2/06 |
| WO | 9819631 | 5/1998 | ............ A61F/2/06 |
| WO | 9819632 | 5/1998 | ............ A61F/2/06 |
| WO | 9819634 | 5/1998 | ............ A61F/2/06 |
| WO | 9819636 | 5/1998 | ............ A61F/2/06 |
| WO | 9819732 | 5/1998 | .......... A61M/25/01 |
| WO | 9838939 | 9/1998 | .......... A61B/19/00 |
| WO | 9838941 | 9/1998 | .......... A61B/19/00 |
| WO | 9838942 | 9/1998 | .......... A61B/19/00 |
| WO | 9848733 | 11/1998 | ............ A61F/2/06 |

* cited by examiner

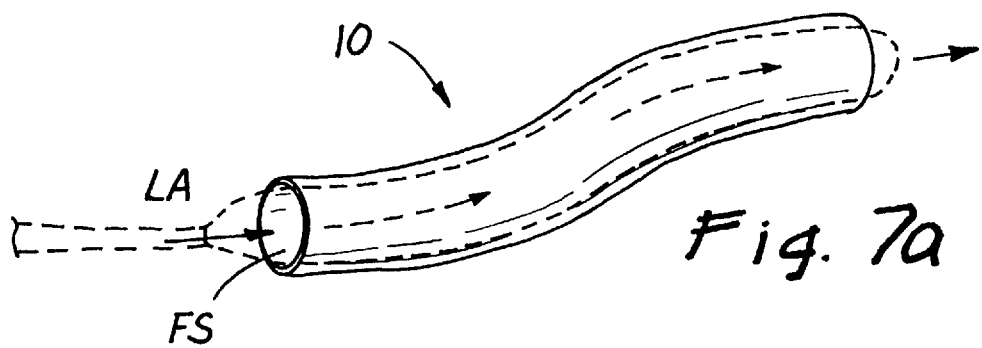
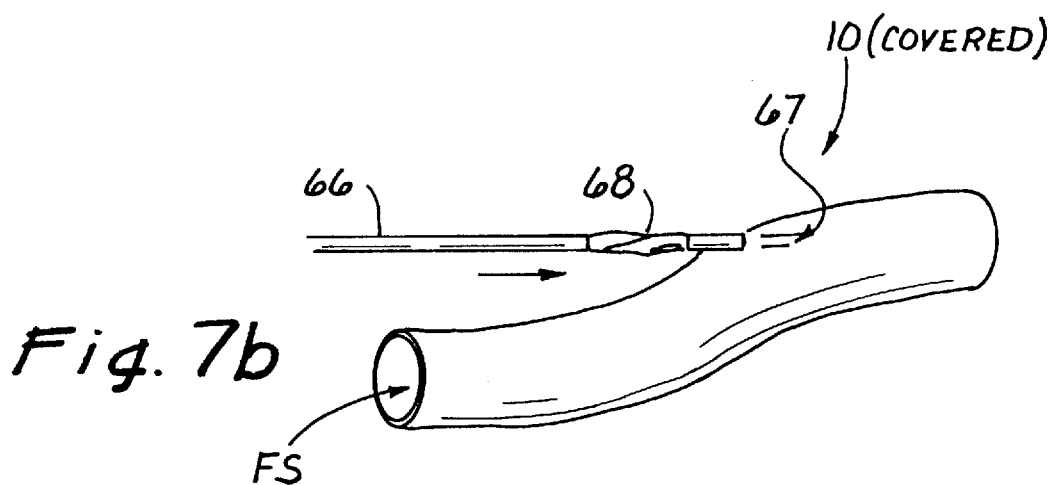
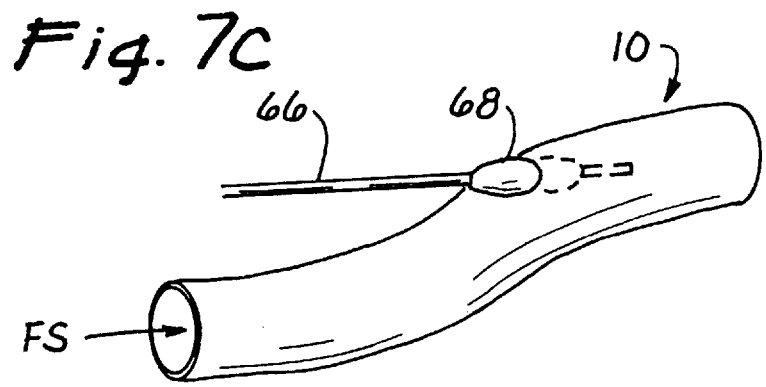

US 6,432,127 B1

DEVICES FOR FORMING AND/OR MAINTAINING CONNECTIONS BETWEEN ADJACENT ANATOMICAL CONDUITS

RELATED APPLICATIONS

This application is a continuation-in-part of co-pending PCT International Application No. PCT/US97/01468 filed on Jan. 31, 1997, and of co-pending U.S. patent application Ser. No. 08/730,327 filed on Oct. 11, 1996 pending and Ser. No. 08/730,496 filed on Oct. 11, 1996 now U.S. Pat. No. 5,830,222. The entire disclosure of each such related application is expressly incorporated herein by reference.

FIELD OF THE INVENTION

The present invention relates generally to medical devices and methods, and more particularly to devices and methods for forming connections or facilitating flow between openings formed in adjacently situated anatomical conduits.

BACKGROUND OF THE INVENTION

In modem medical practice, it is sometimes desirable to form flow-through connections (e.g., passageways or flow channels) between adjacent anatomical conduits (natural or prosthetic), or between adjacent segments of a single anatomical conduit. The types of natural and prosthetic anatomical and conduit(s) which may be linked by such flow-through connections include; blood vessels, vas deferens, fallopian tubes, intestines, lymphatic ducts, grafts, etc.

In particular, U.S. patent application Ser. Nos. 08/730,327 and 08/730,496 have described certain methods and devices for performing transluminal, catheter-based, bypass procedures wherein flow-through connections are formed between two adjacently situated anatomical conduits (e.g., blood vessels) to bypass a diseased, injured or obstructed segment of one of those anatomical conduits, using a segment of the adjacent conduit as the bypass loop. These procedures include catheter based, transluminal, in situ coronary vein bypass procedures wherein at least one primary flow-through connection (i.e., bloodflow passageways) is formed between an obstructed coronary artery and an adjacent coronary vein, such that blood will flow from the obstructed artery into the adjacent coronary vein. The arterial blood which has flowed into the coronary vein may then be allowed to retroperfuse the ischemic myocardium by retrograde flow through the coronary vein. Or, alternatively, one or more secondary flow-through connections may be formed between the coronary vein and the obstructed artery at site(s) downstream of the obstruction (or some other coronary artery), thereby allowing the arterial blood which had flowed into the coronary vein to reenter the obstructed artery (or some other coronary artery), after having bypassed the arterial obstruction.

Also, International Patent Publication No. WO 97/27897 describes certain thoracoscopic or minimally invasive methods for by-passing an obstructed coronary artery by maneuvering, into juxtaposition with the obstructed artery, a tubular graft. Openings are formed in the juxtapositioned graft and in the adjacent artery, at sites upstream and downstream of the obstruction. The graft is then connected to the artery such that the openings in the graft are positioned in alignment with, and in fluidic connection with, the openings in the artery. Blood may then flow through the flowthrough connections between the tube graft and the artery, thereby bypassing an obstructed region of the artery.

Additionally, U.S. Pat. No. 3,042,021 (Read), entitled Bypass Type Insert Plug For Body Passageway, describes a procedure wherein an apparatus is used to connect or facilitate flow between openings formed in adjacent anatomical passageways (e.g., genitourinary ducts), which are situated in side-to-side juxtaposition.

Also, U.S. Pat. No. 5,443,497 (Venbrux), entitled Purcutaneous Prosthetic ByPass Graft and Method of Use, describes a device for bypassing an occluded lumen or for coupling two lumens, and related methods for installing such device(s) within the body.

At least some of the previously described procedures for forming flow-through connections (e.g., passageways or flow channels) between adjacent anatomical conduits may be accomplished by a transluminal, catheter-based approach which avoids the need for open surgical exposure and dissection of the involved anatomical passageways. Such transluminal procedures generally require the passage of a flexible cannula or catheter through the lumen of one of the involved body passageways, deploying or actuating a tissue penetration element from the catheter, through the wall of the passageway in which the catheter is positioned, and into the adjacent passageway to which the side to side connection is to be made. In at least some of these transluminal, catheter-based procedures, it is additionally desirable to install a connector apparatus to maintain the desired alignment of the flow-through openings in the adjacent anatomical conduits, and/or to prevent the leakage of body fluid into the surrounding tissues or spaces. Some connector apparatus of this type have previously been described in U.S. patent application Ser. Nos. 08/730,327 and 08/730,496 as well as International Patent Publication No. WO 97/27898 entitled "Methods and Apparatus for Connecting Openings Formed in Adjacent Blood Vessels or Other Anatomical Conduits". However, none of these previously described methods or apparatus appear to be of optimal design for all clinical applications.

Accordingly, there exists a need in the art for the design and development of new apparatus for connecting or maintaining alignment of flow-through openings formed in adjacent blood vessels or other anatomical conduits. It is further desirable that such connector apparatus be implantable by a transluminal, catheter-based technique to avoid the need for open surgical exposure of the affected anatomical conduits.

SUMMARY OF THE INVENTION

The present invention includes devices and methods for connecting, or facilitating flow between, adjacently situated anatomical or prosthetic conduit(s) (e.g., openings in separate anatomical conduits or two openings at different locations in the same anatomical conduit). The connector devices of the present invention include certain "two-annular-member" embodiments and "three-annular-member" embodiments, as described more fully herebelow.

In accordance with the invention, there is provided a two-annular-member connector device which is implantable within the body of a mammal to facilitate flow between (i.e, to maintain alignment and/or connection between) a first opening formed in an anatomical conduit (e.g., a first blood vessel), and a second opening formed in an anatomical conduit (e.g., an opening formed in a second blood vessel or a second opening formed in the first blood vessel). This two-annular-member connector device generally comprises (a) at least one proximal radially expandable annular member, (b) at least one distal radial expandable annular member, (c) at least one strut member connected to and extending between the proximal and distal annular members. Prior to implantation in the body, this two-annularmember connector device is disposed in a collapsed disposition with its proximal and distal annular members in their radially collapsed configurations and its strut member(s) in a pre-expansion configuration. In this collapsed disposition, the connector device is sufficiently compact to be mounted upon or within a delivery catheter which is transluminally advancable to site of intended implantation. After the delivery catheter has been transluminally advanced to the site of intended implantation, the connector device is released or separated from the delivery catheter, its proximal and distal annular members are expanded to their radially expanded configurations, and its strut member(s) caused or permitted to assume a post-expansion (i.e., curved) configuration. In this manner the connector device may be implanted with its proximal annular member(s) at a first location in an anatomical or prosthetic conduit (e.g., a first blood vessel), its distal annular member(s) at a second location in an anatomical or prosthetic conduit (e.g., a second blood vessel or a second location within the first blood vessel), and its strut member(s) extending therebetween. When so implanted, the two-annular-member connector device may serve to maintain the patency, alignment and/or approximation of the first and second openings—and of any interstitial tunnel, passageway or bypass conduit created or disposed between such openings.

Further in accordance with the invention, there is provided a three-annular-member connector device which is implantable within the body of a mammal to facilitate flow between (i.e, to maintain alignment and/or connection between) a first opening formed in an anatomical conduit (e.g., a first blood vessel), and a second opening formed in an anatomical conduit (e.g., an opening formed in a second blood vessel or a second opening formed in the first blood vessel). This three-annular-member connector device generally comprises (a) at least one proximal radially expandable annular member, (b) at least one distal radially expandable annular member, (c) at least one medial radially expandable annular member, (d) at least one first strut member connected to and extending between the proximal and medial annular members, and (e) at least one second strut member connected to and extending between the medial and distal annular members. This device is initially mountable upon or in a deliver catheter while in a collapsed disposition wherein the proximal, distal and medial annular members are in radially compact configurations and the strut members are in "pre-expansion" configurations. Thereafter the device is transitioned to an implantation disposition wherein the proximal, distal and medial annular members are in their radially expanded configurations and the strut member(s) are in their "post-expansion" (e.g., curved) configurations. This results in the connector device being implanted with its proximal annular member(s) at a first location in an anatomical or prosthetic conduit (e.g., within a first blood vessel), its distal annular member(s) at a second location in an anatomical or prosthetic conduit (e.g., within a second blood vessel or a second location within the first blood vessel), and its medial annular member(s) located within or between the first and second openings of the anatomical or prosthetic conduit(s). When so implanted, the three-annular-member connector device may serve to maintain the patency, alignment and/or approximation of the first and second openings—and of any interstitial tunnel, passageway or bypass conduit created or disposed between such openings.

Still further in accordance with the invention, in either the two-annular-member or three-annular-member connector devices, the actual number of annular members present (i.e., in excess of two (2) or three (3)) may be determined by functional considerations, such as the amount of scaffolding of support required to maintain the desired patency and approximation of the flow channels, and/or the specific position at which the device is to be implanted within the body.

Still further in accordance with the invention, any embodiment of the connector device of the present invention may be fully or partially covered by a pliable covering (e.g., woven polyester, expanded polytetrafluoroethylene (ePTFE), polyurethane, etc.) to channel, direct, block, or otherwise control the flow of body fluid and/or to improve the biological compatibility of the connector device. Additionally or alternatively, such covering may be formed of material which will promote or prevent proliferation of the adjacent tissue. In some applications, the covering may be formed of material which will biodegrade or become absorbed after it has served its intended purpose. Flow through holes or openings may be formed at selected locations in such pliable covering to direct or permit the desired flow of body fluid through the device. Such flow-through holes or openings may be formed in the covering prior to implantation of the connector device, or may be formed in situ following implantation of the connector device.

Still further in accordance with the present invention, the annular members and/or strut member(s) of the connector devices may be formed of a resilient material which is initially compressible and constrainable such that the annular members are in their radially collapsed states and the strut member(s) are in their pre-expansion configurations but which, when unconstrained, will self-expand to a configuration wherein the annular members are expanded and the strut member(s) are in their post-expansion configurations. Alternatively, the annular members and/or strut member(s) of the connector devices may be formed of a malleable (e.g., plastically deformable) material which is initially formed such that the annular members are in their radially collapsed states and the strut member(s) are in their pre-expansion configurations but which, when outward radial pressure is exerted thereagainst, will plastically deform to a configuration wherein the annular members are expanded and the strut member(s) are in their post-expansion configurations.

Still further in accordance with the invention, the connector devices may be implanted in various different orientations or arrangements and/or my be purposely formed or deformed in a manner which will exert a traction force upon the surrounding tissue. Such traction force may be utilized to cause sloping or curvature of the openings formed in the first and second anatomical conduits and/or any surrounding tissue, to promote non-turbulent, laminar flow of blood or other body fluid between the anatomical conduits. In this regard, the invention includes methods (described in detail herebelow), for placing the connector devices in opposing orientations so as to cause two (2) adjacent interstitial passageways to angle or slope toward one another to promote non-turbulent flow therethrough.

Further aspects and advantages of the present invention will be apparent to those skilled in the art, after reading and understanding the detailed description of preferred embodiments set forth herebelow, and after viewing the accompanying drawings.

BRIEF DESCRIPTION OF THE DRAWINGS

FIG. 6b' is a cross-sectional view of the device of FIG. 6b showing a portion of a pliable covering extending transversely thereacross;

FIGS. 7a–7e are step-wise schematic showings of a method for in situ formation of the flow-through openings in the covered connector device of FIG. 6, after the connector device has been implanted within adjacent anatomical conduits.

DETAILED DESCRIPTION OF THE PREFERRED EMBODIMENTS

The following detailed description and the accompanying drawings are provided for purposes of describing and illustrating presently preferred embodiments and/or examples of the invention only, and are not intended to limit the scope of the invention in any way.

Figure 1A:
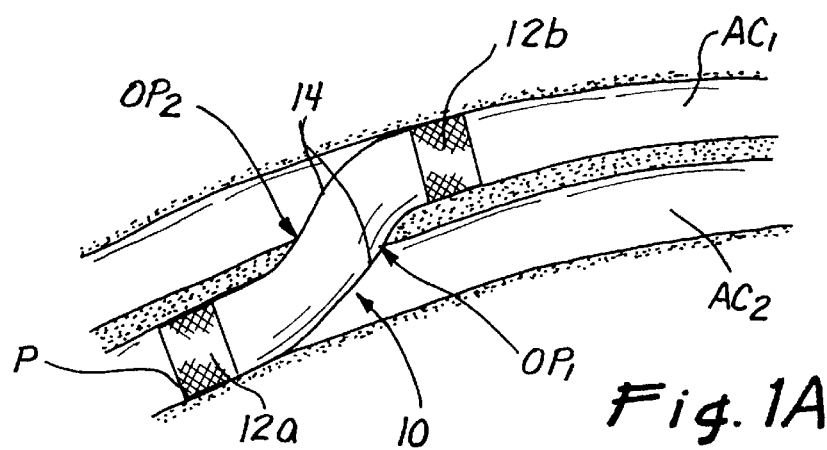
FIG. 1a is a schematic showing of adjacent anatomical conduits which have an interstitial passageway formed therebetween and a two-annular member connector device of the present invention disposed therewithin.

A. Structure and Function of the Two-Annular Member and Three-Annular Member Connector Devices FIG. 1a shows, in schematic fashion, a two-annular member connector device 10 of the present invention operatively implanted so as to maintain connection between a first opening $OP_1$ formed in the wall of a first anatomical conduit $AC_1$ and a second opening $OP_2$ formed in the adjacent wall of a second anatomical conduit $AC_2$. This two-annular member connector device 10 generally comprises proximal and distal radially expandable annular members 12a, 12b having a plurality of strut members 14 extending therebetween. As shown, the proximal annular member 12a may be positioned within the lumen of the first anatomical conduit $AC_1$ so as to frictionally engage the surrounding wall of that anatomical conduit $AC_1$, the distal annular member 12b is positioned within the lumen of the second anatomical conduit $AC_2$ so as to frictionally engage the surrounding wall of that anatomical conduit $AC_2$, and the strut members 14 extend through the respective first and second openings $OP_1$, $OP_2$. In this manner, the connector device 10 forms a connection between the first and second anatomical conduits $AC_1$, $AC_2$ and maintains the first and second openings $OP_1$, $OP_2$ in alignment with one another such that body fluid (e.g., blood) may flow therethrough.

Figure 1B:
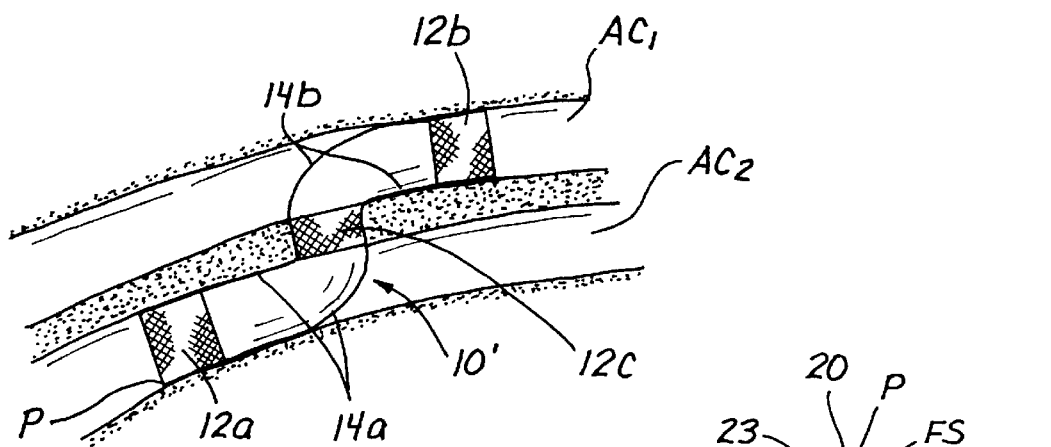
FIG. 1b is a schematic showing of adjacent anatomical conduits which have an interstitial passageway formed therebetween and a three-annular member connector device of the present invention disposed therewithin.

FIG. 1b shows, in schematic fashion, a three-annular member connector device 10' of the present invention operatively implanted so as to maintain connection between a first opening $OP_1$ formed in the wall of a first anatomical conduit $AC_1$, and a second opening $OP_2$ formed in the adjacent wall of a second anatomical conduit $AC_2$. This three-annular member connector device 10' generally comprises proximal, distal and medial radially expandable annular members 12a, 12b, 12c. A plurality of first strut members 14a extend between the proximal annular member 12a and the medial annular member 12c. A plurality of second strut members 14b extend between the medial annular member 12c and the distal annular member 12b. As shown, the proximal annular member 12a may positioned within the lumen of the first anatomical conduit $AC_1$ so as to frictionally engage the surrounding wall of that anatomical conduit $AC_1$, the distal annular member 12b is positioned within the lumen of the second anatomical conduit $AC_2$ so as to frictionally engage the surrounding wall of that anatomical conduit $AC_2$, and the medial annular member 12c is positioned within the passageways or openings $OP_1$, $OP_2$ formed in the walls of the adjacent anatomical conduits $AC_1$, $AC_2$ and/or within any intervening tissue (e.g., connective tissue, muscle, etc.) which may reside between the first and second anatomical conduits $AC_1$, $AC_2$. In this manner, the three-annular member connector device 10' forms a connection between the first and second anatomical conduits $AC_1$, $AC_2$ and maintains the first and second openings $OP_1$, $OP_2$ in alignment with one another such that body fluid (e.g., blood) may flow therethrough. Additionally, in this three-annular-member embodiment, the medial annular member 12c provides additional scaffolding or support for tissue which surrounds the first and second openings $OP_1$, $OP_2$ to maintain patency of the flow-through passageway and/or may act as a bulkhead or barrier to deter or prevent body fluid (e.g., blood) from infiltrating or leaking into the region between the adjacent anatomical conduits $AC_1$, $AC_2$.

The two-annular-member connector device 10 or the three-annular-member connector device 10' may be formed at least partially of resilient material which is preformed and biased to a curvilinear shape (e.g., a serpentine shape having a first curve in one direction and a second curve in another direction) as shown in FIGS. 1a and 1b. Alternatively such devices 10, 10' may be of a flexible or hinged construction which will allow them to assume the desired curved (e.g., serpentine) configuration when implanted. Also, as shown in FIG. 11e and described more fully herebelow, the two-annular-member connector device 10 may be preformed to a multicurvate shape wherein the struts 14 are preformed or formable to a generally "U" shaped configuration such that the proximal and distal annular members 12a, 12b may reside at spaced apart locations in the first anatomical conduit $AC_1$, and the strut members 14 extend through the first and second passageways or openings $OP_1$, $OP_2$ and through the adjacent segment of the second anatomical conduit (e.g., a vein which lies adjacent to an obstructed artery) which is being used as an in situ bypass conduit.

Figure 1C:
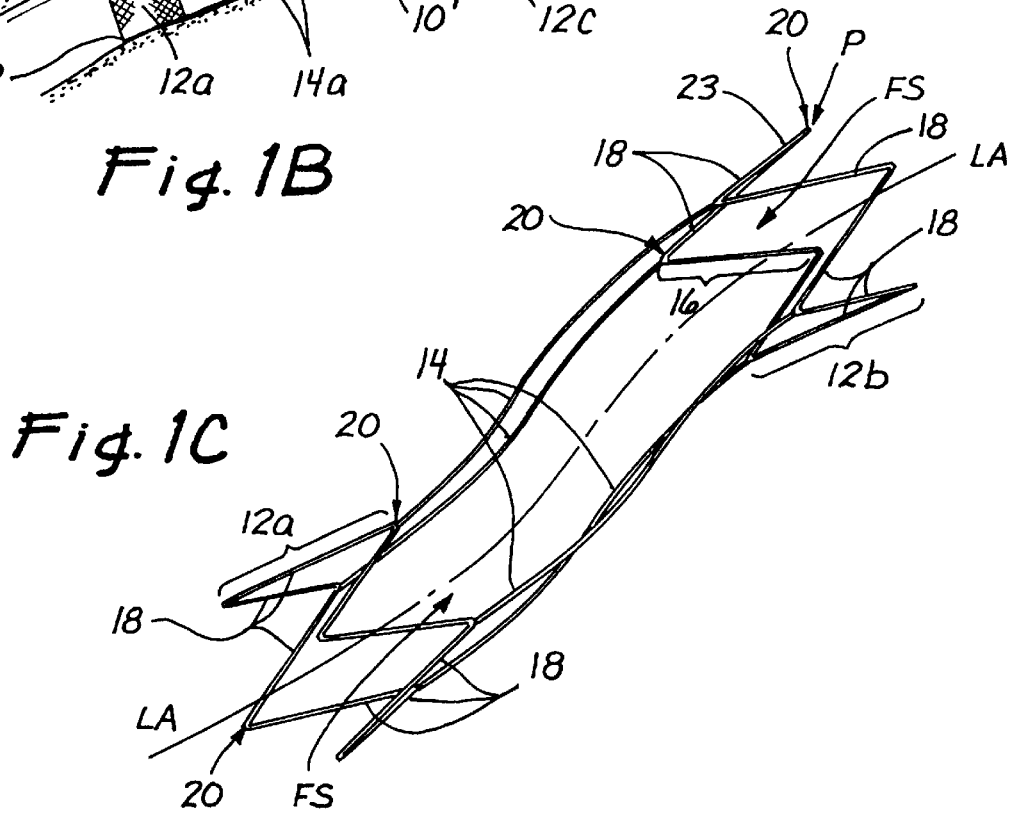
FIG. 1c is a perspective view of a two-annular-member connector device of the present invention in a fully assembled, operative configuration.

FIG. 1c is a more detailed showing of the preferred two-annular-member connector device 10 of FIG. 1a. In this preferred embodiment, the proximal and distal annular members 12a, 12b comprise alternating (e.g., zig-zag or sinusoidal) elongate members 16 which, when in their radially expanded configuration, have linear portions 18 and apices 20 which define a generally cylindrical annular shape. Four (4) strut members 14 are included in this embodiment. The opposite ends of each strut member 14 are connected to the inboard apices 20 of the alternating elongate members 16 which make up each annular member 12a, 12b, as shown. In this manner, the strut members 14 combine with the alternating elongate members 16 to define a longitudinal flow-through space FS through which a biological fluid (e.g., blood) may flow. A longitudinal axis LA is projectable through this device, when in its radially expanded implantation configuration, as shown in FIG. 1c.

Figure 1D:
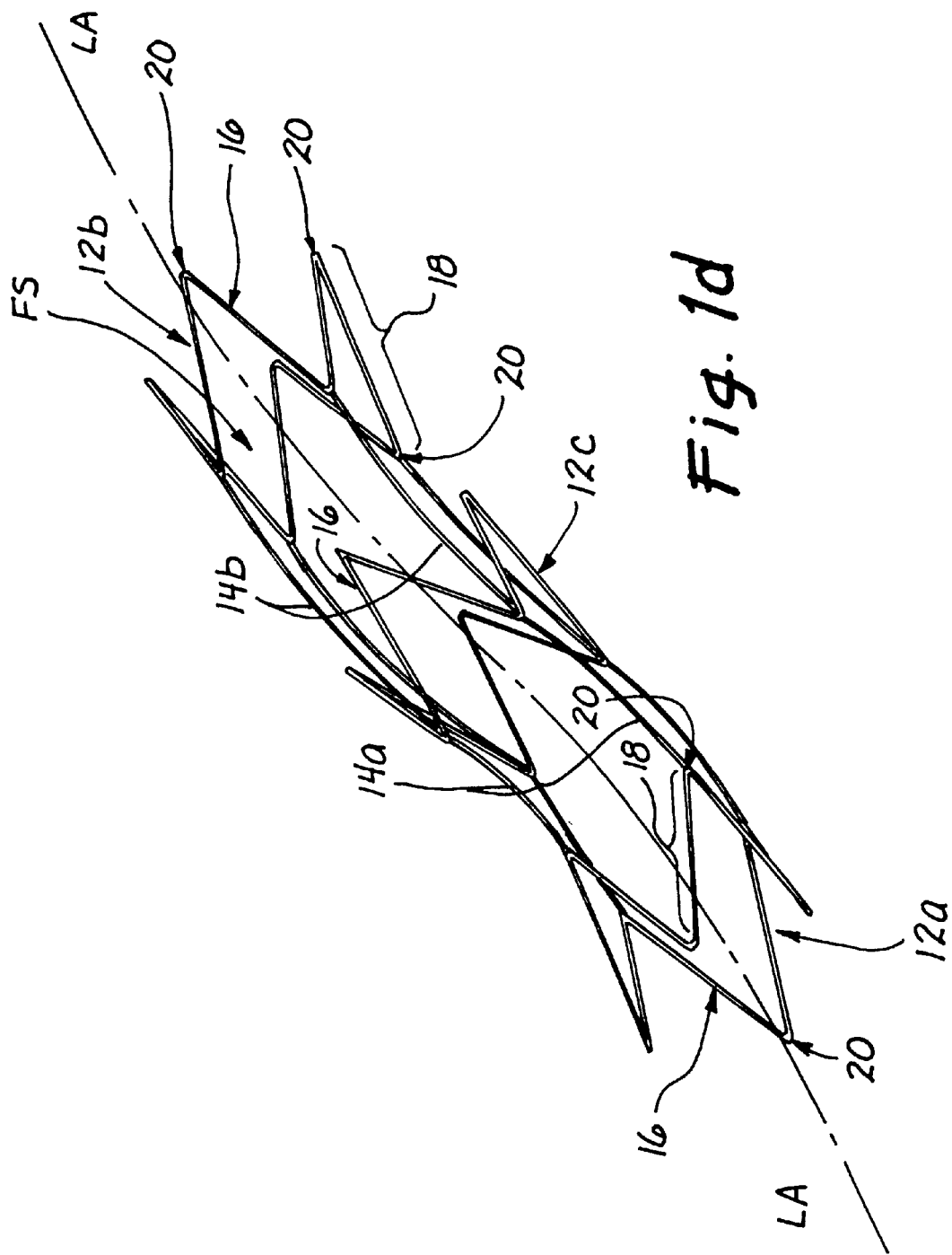
FIG. 1d is a perspective view of a three-annular-member connector device of the present invention in a fully assembled, operative configuration.

FIG. 1d is a more detailed showing of the preferred three-annular-member connector device 10 of FIG. 1b. In this preferred embodiment, the proximal, distal and medial annular members 12a, 12b, 12c comprise alternating (e.g., zig-zag or sinusoidal) elongate members 16 which, when in their radially expanded configuration, have linear portions 18 and apices 20 which define a generally cylindrical annular shape. Four (4) strut members 14 are included in this embodiment. The opposite ends of the strut members 14a, 14b are connected to the adjacent apices 20 of the alternating elongate members 16 which make up each annular member 12a, 12b, 12c, as shown. In this manner, the strut members 14a, 14b combine with the alternating elongate members 16 to define a longitudinal flow-through space FS through which a biological fluid (e.g., blood) may flow. A longitudinal axis LA is projectable through this device, when in its radially expanded implantation configuration, as shown in FIG. 1d. It should also be appreciated that by varying the width of the strut members 14, the amount of radial force imparted by the strut members 14 against the tissue can be varied in accordance with the amount of force required to maintain patency of the flowpath in the subject anatomy.

Figure 2:
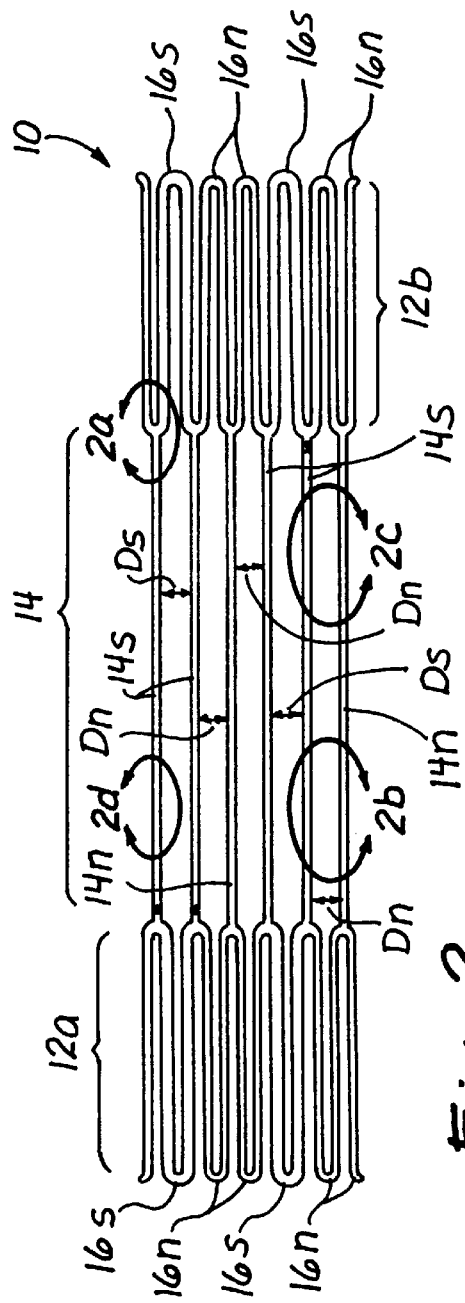
FIG. 2 is a plan view of a preferred two-annular member connector device of the present invention disposed in a flattened, pre-assembly configuration.
Figure 3:
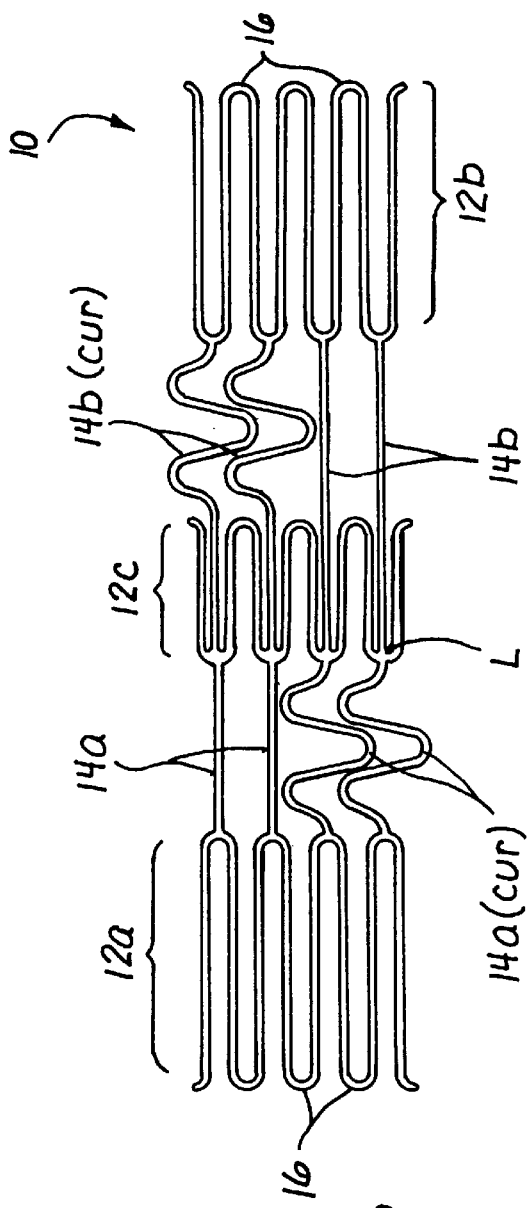
FIG. 3 is a plan view of a preferred three-annular member connector device of the present invention, disposed in a flattened, pre-assembly configuration.

The connector devices 10, 10' may be fabricated in any suitable way, of any suitable material. For example, the connector devices 10, 10' may be cut (e.g., laser cut) from a solid, cylindrical tube, or they may be fabricated from wire or other suitable strand-like material. FIGS. 2 and 3 show flattened views of specific connector devices 10, 10' of the present invention, which have been cut from a solid, cylindrical tube by presently known laser cutting technology. The tube is preferably formed of resilient or superelastic material, such as a nickel- titanium alloy containing 50.8 atomic % nickel/balance titanium.

The showings of FIGS. 2 and 3 depict preferred connector devices 10, 10' in their radially compact configurations after having undergone a hypothetical flattening maneuver—i.e., a maneuver whereby a straight cut is formed longitudinally in each device 10, 10a, and the device 10, 10' is then unrolled from its original cylindrical configuration to a flat configuration.

In the embodiment shown in FIG. 2, some of the alternating elongate members 16s (i.e., the "selected" alternating elongate members) of each annular member 12a, 12b may be wider in cross-dimension and/or of greater mass than the other alternating elongate members 16n (i.e., the "non-selected" alternating elongate members). Because the selected alternating elongate members 16s are wider and/or of greater mass than the other non-selected alternating elongate members 16n, the selected alternating elongate members 16s will diverge (i.e., separate or spread) further away from each other than will the non-selected alternating members 16n, as the device 10 or 10' self-expands to its radially expanded configuration. As a result, the corresponding selected strut members 14s which are attached to the apices 20s of the selected alternating elongate members 16s, will also separate further apart than the other non-selected strut members 14n. Thus, when the device 10 is in its radially expanded implantation configuration, the separation distance $D_s$ between the selected struts 14s will be greater than the separation distance $D_n$ between non-selected struts 14n. In this manner, the device 10 may be implanted in a specific rotational orientation wherein the intended flow of blood or other body fluid will pass between the selected struts 14s and the increased separation distance $D_s$ therebetween will minimize the frictional drag or disruption of flow which would or could occur if the selected struts 14s were within the fluid flow path. Although this aspect of the invention is shown in relation to FIG. 2, it will be appreciated that this aspect of the invention may be incorporated into any embodiment of the two-annular member or three-annular member connector device 10, 10' wherein the structure of the device will permit.

Figure 2A:
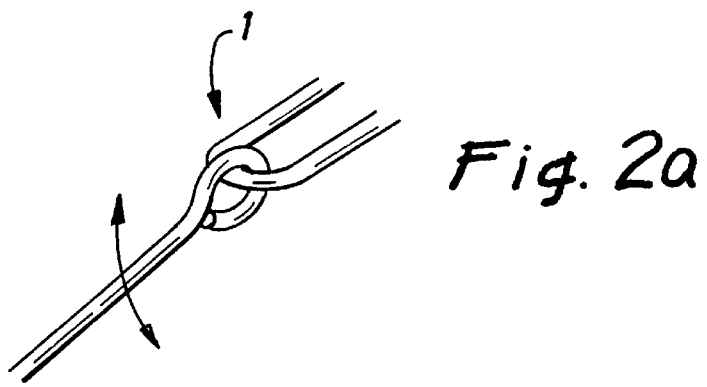
FIG. 2a is an enlarged perspective view of segment 2a of FIG. 2, showing an alternative hinged connection formed between the strut members and the annular member component(s) of the connector device.

The strut members 14 may be rigidly connected to (e.g., formed continuously with or fused to) the inboard apices 20 of the annular members 12a, 12b as shown in FIG. 2, or alternatively such strut members 14 may be flexibly connected to (e.g., connected by hinged or pivotal connection) to the inboard apices 20 as shown in FIG. 2a. In embodiments wherein the strut members 14 are rigidly connected to the inboard apices 20, it will be desirable for the strut members to be formed or formable to a curved (e.g. serpentine) shape which conforms to the shape of the surrounding anatomy at the intended site of implantation. In other embodiments wherein the strut members 14 are flexibly connected to the inboard apices 20, the strut members may be formed or formable to a straight or minimally curved configuration to facilitate transluminal delivery of the device 10, as these flexible connections between the strut members 14 and annular members 12a, 12b will automatically pivot or flex so as to conform to the shape of the surrounding anatomy within which the device 10 is implanted. Although this aspect of the invention is shown in relation to FIG. 2, it will be appreciated that this aspect of the invention may be incorporated into any embodiment of the two-annular member or three-annular member connector device 10, 10' wherein the structure of the device will permit.

Figure 2B:
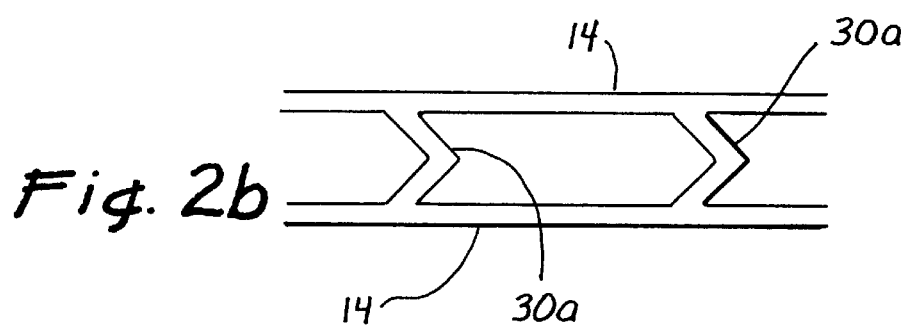
FIG. 2b is an enlarged perspective view of segment 2b of FIG. 2, showing optional interconnecting members of a first type formed between adjacent strut members of the connector device.
Figure 2C:
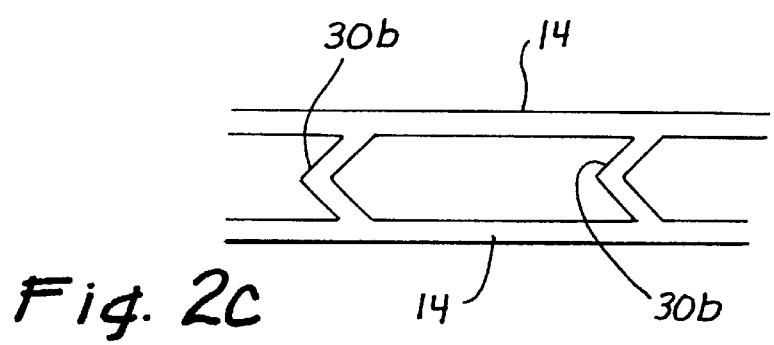
FIG. 2c is an enlarged perspective view of segment 2c of FIG. 2, showing optional interconnecting members of a second type formed between adjacent strut members of the connector device.

Also, as shown in FIGS. 2b and 2c, some or all of the strut member(s) 14 may be connected to neighboring strut member(s) 14 by linking members 30a or 30b. These linking members 30a, 30b may serve to selectively control or limit the distance of separation Ds or Dn of the adjacent strut members 14 and/or may provide increased scaffolding to prevent surrounding tissue (e.g., intervening connective tissue or muscle which resides between the anatomical conduits) from lapsing, invading or ingrowing into the flow-through space FS. As shown in FIGS. 2b and 2c these linking members 30a, 30b may be of curved or V-shaped configuration, and those linking members 30a in one portion (e.g., the proximal half) of the connector device 10 may be directed in a direction X, which is opposite the direction Y in which those linking members 30b in another portion of the connector device (e.g., the distal half) are directed. The acute internal angle of each such "V" shaped linking member 30a, 30b will decrease as the separation distance Ds between the adjacent strut members 14 increases. Although this aspect of the invention is shown in relation to FIG. 2, it will be appreciated that this aspect of the invention may be incorporated into any embodiment of the two-annular member or three-annular member connector device 10, 10' wherein the structure of the device 10, 10' will permit.

Figure 2D:
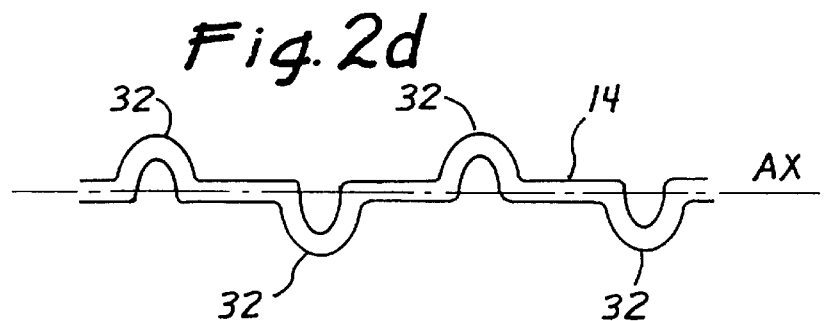
FIG. 2d is an enlarged perspective view of segment 2d of FIG. 2, showing optional curved regions formed in the strut members of the connector device to provide for adjustability in length of the device.

Also, as shown in FIG. 2d, some or all of the strut members 14 may incorporate spaced-apart curved segments 32 which diverge laterally from the longitudinal axis $AX_{strut}$ of the strut 14. These curved segments 32 may be arcuate (e.g., generally U shaped) and may be spaced equidistantly from one another. These curved segments 32 provide increased scaffolding to prevent surrounding tissue (e.g., intervening connective tissue or muscle which resides between the anatomical conduits) from lapsing, invading or ingrowing into the flow-through space FS.

In the preferred connector device 10' shown in FIG. 3, the strut members 14b which extend from the distal annular member 12b pass longitudinally through the medial annular member 12c and are attached thereto at locations L on the proximal aspect of the medial annular member 12c, thereby causing the structure of the medial annular member 12c to be more dense (i.e., less porous) than the proximal or distal annular members 12a, 12b. Such increased density of the medial annular member will provide a regionalized increase or concentration of scaffolding to prevent tissue which surrounds the medial annular member 12c (e.g., intervening connective tissue or muscle which resides between the anatomical conduits) from lapsing, invading or ingrowing into the flow-through space FS which passes through the medial annular member 12c. This optional aspect of the invention may be particularly desirable in applications where the tissue which surrounds the medial annular member 12c is likely to undergo proliferation (e.g., formation of granulation tissue) or in-growth which could occlude or decrease the patency of the flow space FS. Although this aspect of the invention is shown specifically in relation to FIG. 2, it will be appreciated that this aspect of the invention may be incorporated into any embodiment of the two-annular-member or three-annular-member connector device 10, 10' wherein the structure of the device 10, 10' will permit.

As also shown in FIG. 3, in some embodiments of the invention, some of the strut members 14a (crv), 14b (crv) may be longer than the other strut members 14a, 14a, and may incorporate one or more waves or curves while in their pre-expansion configuration. These strut members 14a (crv), 14b (crv) will typically be required to navigate a larger radius of curvature than the other strut members 14a, 14b which are located laterally across from them. Thus, these strut members 14a (crv), 14b (crv) have a curve or wave form built in while in their pre-expansion configurations, and such curve or wave form will elongate (e.g., relax or become shallower) as the device 10 transitions to its expanded, implantation configuration and the excess length of those strut members 14a (crv), 14b (crv) which become elongated will accommodate the increased radius of curvature which they are required to navigate as device 10 is implanted.

B. Methods and Devices for Precise Rotational Orientation of Delivery Catheter Used for Implantation of Connector Devices Having Preformed Curved Configuration In embodiments of the invention wherein the connector device 10, 10' has a preformed, curved configuration as shown in FIG. 1c, it will often be desirable to preposition the delivery catheter used to deliver the connector device 10, 10' in a specific rotational orientation to ensure that the connector device 10, 10' will be properly oriented when it is expelled from the delivery catheter 48.

i. Marker(s) on Delivery Catheter

Markers on the delivery catheter 48 may be specifically positioned and/or configured to provide an indication of the longitudinal placement of the connector 10, 10' within the catheter. Such markers may then be utilized as the delivery catheter 48 is placed across the passageway between the anatomical conduits, to allot the operator to determine where the ends of the connector device 10, 10' will ultimately be placed when the device 10, 10' is implanted.

Figure 4A:
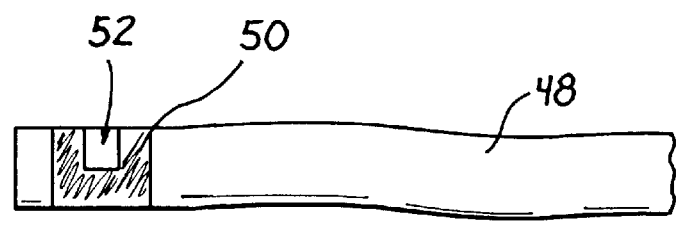
FIG. 4a is a side elevational view of a delivery catheter marker of the present invention disposed in a first rotational orientation, accompanied therebeneath by a schematic showing of a connector device of the present invention in a corresponding first rotational orientation.
Figure 4B:
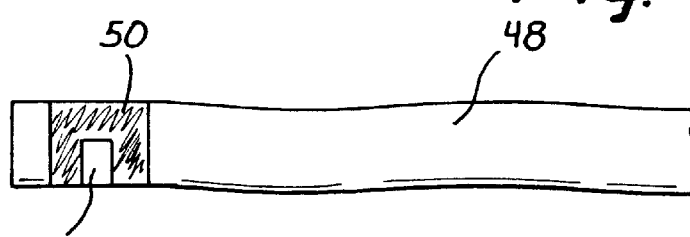
FIG. 4b is a side elevational view of a delivery catheter marker of the present invention disposed in a first rotational orientation, accompanied therebeneath by a schematic showing of a connector device of the present invention in a corresponding third rotational orientation.
Figure 4C:
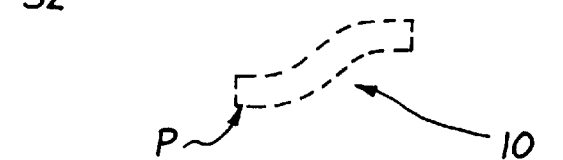
FIG. 4c is a side elevational view of a delivery catheter marker of the present invention disposed in a third rotational orientation, accompanied therebeneath by a schematic showing of a connector device of the present invention in a corresponding third rotational orientation.
Figure 4C:
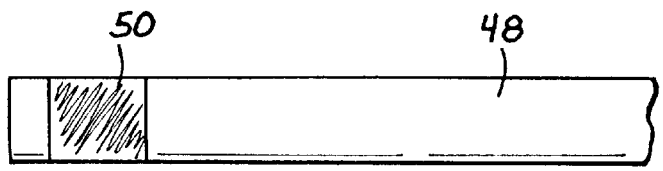

Additionally, the delivery catheter 48 may incorporate at least one marker 50 which indicates the particular rotational orientation in which the connector device 10, 10' has been loaded into the catheter 48. As shown in FIGS. 4a–4c, such marker 50 may comprise a band having a notch 52 formed at a specific location thereon. The band of this marker 50 may be formed of any suitable material capable of being imaged or detected by the type of imaging or detection system being used (e.g., x-ray, fluoroscopy, ultrasound, Doppler, MRI, etc.) For example, the marker 50 may be formed of radiopaque or radiodense metal or plastic which may be imaged by fluoroscopy. The location of the notch 52 signifies or marks a predetermined location or point P on the connector device 10, 10'.

ii. Marker(s) on Connector Device

Figure 5A:
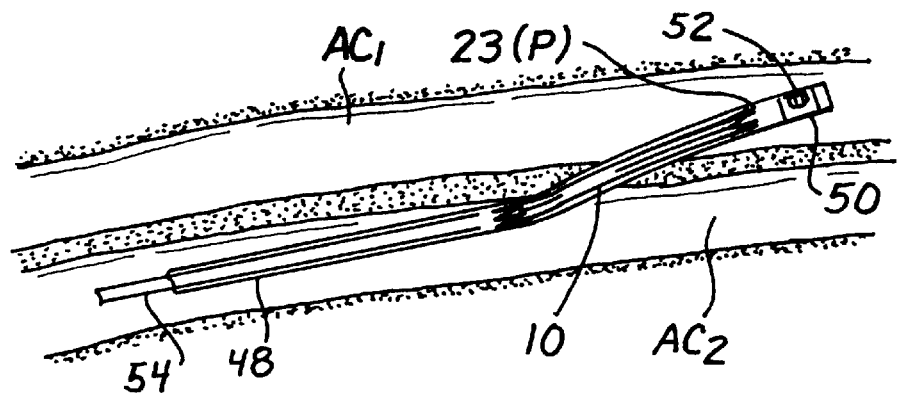
FIGS. 5a–5c are step-wise, schematic showings of a delivery catheter which incorporates a marker of the present invention, being used to deliver a connector device of the present invention to form a connection between adjacently situated anatomical conduits in which openings have been formed.
Figure 5B:
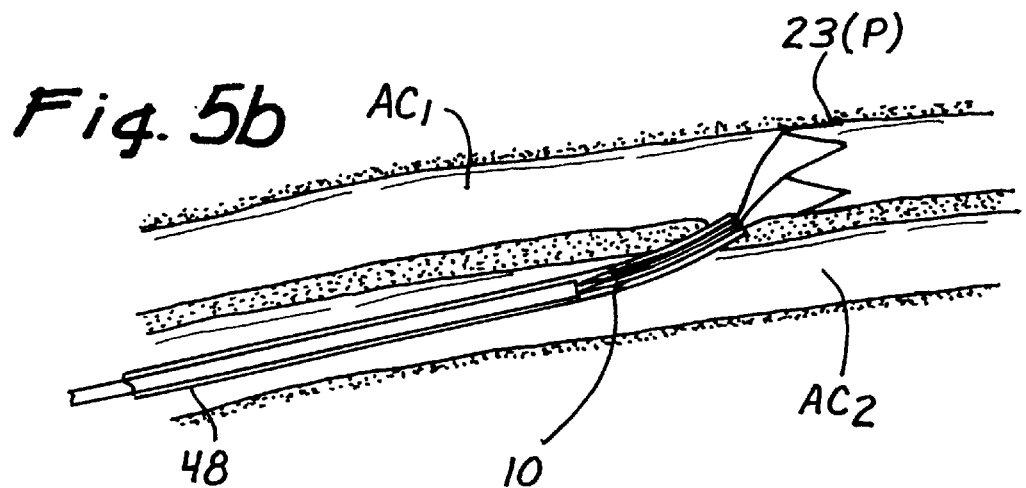
Figure 5C:
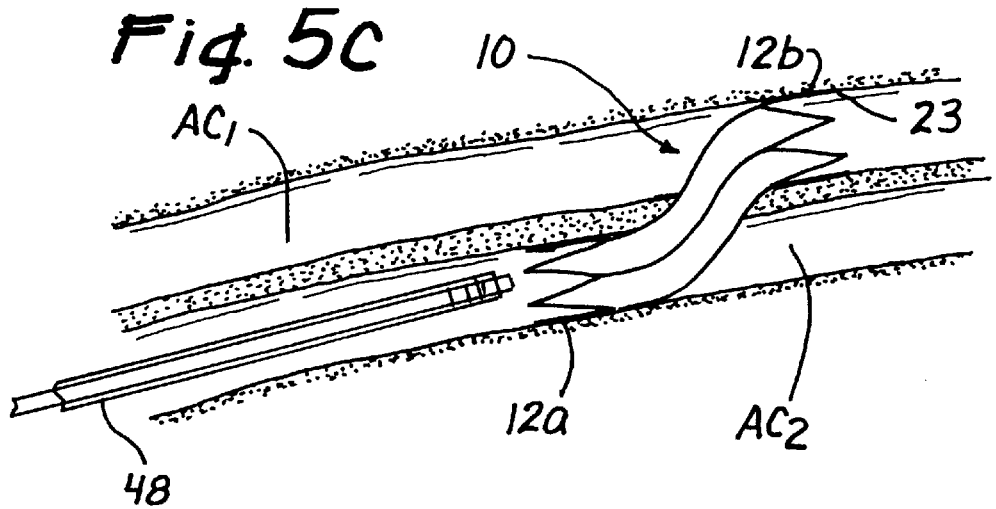

At least one second imageable marker 23 capable of being imaged by the particular imaging system available during the procedure (e.g., x-ray, fluoroscopy, ultrasound, Doppler, MRI, etc.) may be formed on the distal end of the connector device 10, 10' at location P. These markers 23, 50 may then be used by the operator to facilitate implantation of a device 10, 10' having a preformed curvature, in its proper orientation of curvature, as illustrated by FIGS. 5a–5c and described more fully herebelow.

iii. Method for Using Markers to Ensure Correct Rotational Orientation of Preformed Connector Device Prior to Implantation With particular reference to FIGS. 5a–5c, a connector device 10 having strut members 14 which are preformed to a desired curvilinear configuration, is preferably sufficiently resilient to be compressible to a substantially straight, radially compact configuration whereby it may be loaded into the lumen of a delivery catheter 48. When the device 10 is loaded into the delivery catheter 48, a core member 54 will be positioned within and/or behind the device 10 to prevent the connector device 10 from retracting in the proximal direction within the delivery catheter 48.

The connector device 10 having preformed curved strut members 14 may be oriented within the catheter 48 such that the second marker 23 on point P of the connector device 10 is next to the notch 52 of the catheter marker 50. The catheter 48 is then advanced through the lumen of a first anatomical conduit $AC_1$, through previously formed openings $OP_1$, $OP_2$, and into the lumen of the second anatomical conduit $AC_2$, as shown in FIG. 5a. Thereafter, the catheter 48 is rotated under radiographic visualization (e.g., fluoroscopy) until the notch 52 of marker 50 is located adjacent the wall of the second anatomical conduit $AC_2$ directly (i.e., 180 degrees) opposite the location of the second opening $OP_2$. Thereafter the core member 54 is held in longitudinally fixed position the prevent proximal retraction of the connector device 10, and the catheter 48 is slowly retracted in the proximal direction. As the catheter 48 is retracted, the first annular member 12a will initially become uncovered by the catheter 48 such that it may radially expand. As the distal end of the first annular member 12a is uncovered by the retracting catheter 48, the operator may check the position of the marker 23 on the distal end of the device 10 (i.e., on the distal annular member 12a) to confirm that the device 10 is in its desired rotational orientation. If the rotational orientation of the device is determined to be improper, the operator may halt further retraction of the catheter 48 and may make further adjustment of its rotational orientation before the first annular member 12a becomes fully radially expanded. After the proper rotational orientation of the connector device 10, 10' has been confirmed by the positioning of the second marker 23, the catheter 48 will be further retracted such that the curved strut(s) 14 and any third annular member 12c (if present) extend as desired through the openings $OP_1$, $OP_2$ and the second annular member 12b becomes deployed and radially expanded within the lumen of the second anatomical conduit $AC_2$.

Those skilled in the art will recognize that these aspects of the present invention, and particularly the use of visible markers to effect the desired orientation and positioning of the connector device 10 at the time of implantation, may be accomplished in accordance with the catheter-orienting/positioning techniques (e.g., techniques which use an accompanying intravascular ultrasound imaging catheter (IVUS)) described in co-pending U.S. patent application Ser. No. 08/837,294 filed on Apr. 11, 1997, the entire disclosure of such co-pending application being expressly incorporated herein by reference.

C. Full or Partial Covering of Connector Devices

Figure 6A:
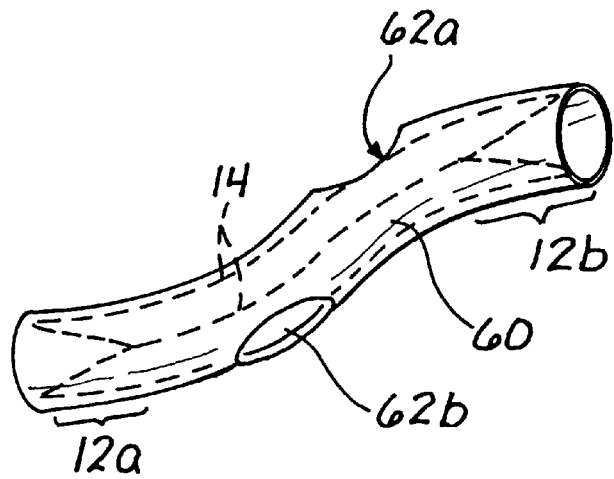
FIG. 6a is a perspective view of a connector device of the present invention having an optional covering formed thereon, with flow-through openings formed at selected locations in the covering.
Figure 6B:
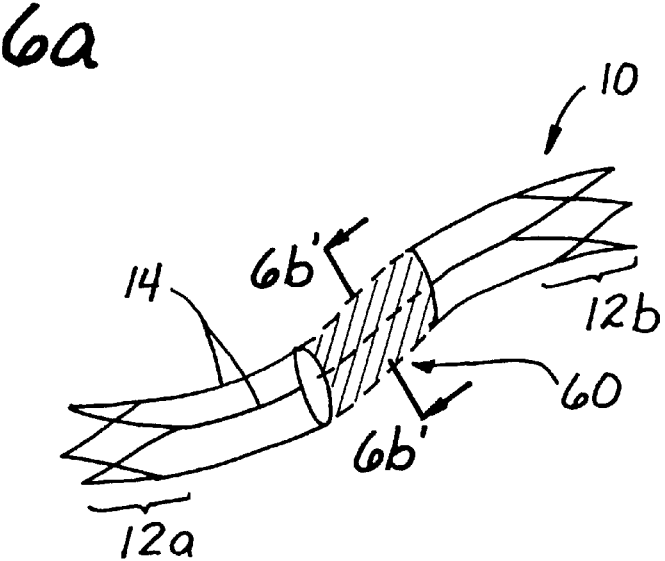
FIG. 6b is a perspective view of a connector device of the present invention having an option partial covering formed thereon, such covering being substantially confined to the mid-portion of the device.
Figure 6B:
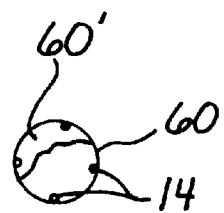

As shown in FIGS. 6a–6b, any of the two-annular-member or three-annular-member connector devices 10 (covered) may be fully or partially covered by a pliable covering 60, 60 (partial). Such covering 60, 60(partial) may be formed of any suitable material, such as a polymer film (expanded polytetrafluoroethylene (ePTFE) or polyurethane) or a fabric (e.g., woven polyester). Such covering 60, 60(partial) may be disposed upon and supported by the annular members 12a, 12b, 12c and/or the strut members 14a, 14b, 14a (crv), 14b (crv). Such covering 60, 60(partial) may form a barrier about all or a portion of the flow space FS defined within the connector device 10 (covered). In this regard, such optional covering 60, 60(partial) may serve to: i) prevent direct contact between the annular members 12a, 12b, 12c and/or strut members 14a, 14b, 14a(crv), 14b(crv) and the adjacent host tissue to i) improve the biocompatability of the connector device 10(covered), ii) minimize the potential for immunologic graft-host responses; iii) prevent body fluid from leaking or infiltrating into spaces or tissues which surround the connector device 10 (covered); iv) channel or direct the flow of body fluid in desired directions or into desired anatomical structures; v) prevent or deter tissue proliferation, ingrowth or invasion of tissue into the flow space FS defined within the connector device 10(covered) and/or vi) distribute any outwardly directed force created by the connector device 10, 10' over the adjacent surface of the anatomical conduit(s), thereby minimizing the potential for localized erosion or perforation of the anatomical conduits by the implanted connector device 10(covered). Also, in some embodiments such as that shown in FIG. 11, the covering 60, 60 (partial) may extend transversely through the device, or may be otherwise positioned, to fully or partially block the flow of body fluid (e.g., blood) in a certain direction or through a certain portion of the device. For example, FIG. 6b' shows a cross-section of the device 10 of FIG. 6b with a portion 60' (shown cut away) of the covering 60 extending transversely across the device.

The physical and material properties of the covering 60, 60 (partial) may vary depending on the intended application and mode of deployment of the device 10 (covered). In some embodiments, the covering 60 may be formed of material which is sufficiently elastic to expand to the radially expanded diameter of the device 10(covered) and to contract to the radially contracted diameter of the device 10(covered) without creating substantial slack in the material of the covering 60. In other embodiments wherein the covering 60 does not have such range of elasticity, it is preferable that the covering 60 be attached to or disposed on the annular members 12a, 12b, 12c and or the strut members 14a, 14b, 14a(crv), 14b(crv) such that any slack which forms when the device 10(covered) is in its radially compact configuration, may be folded, furled or compressed in a manner which will reduce such slack to a small diameter close to or equal to that of the radially compact annular members 12a, 12b, 12c, thereby facilitating the desired transluminal passage of the device 10(covered).

In some embodiments, the fall or partial covering 60, 60 (partial) may be formed of material which is capable of being imaged by the type of imaging system being utilized during the procedure (e.g., x-ray, flouroscopy, MRI, ultrasound, Doppler, etc.). For example, the covering 60, 60(partial) may be impregnated with $BaSO_4$ so as to be radiographically imaged, thereby allowing the operator to place the cover 60, 60(partial) in a desired location, and also allowing the cover 60, 60(partial) to continue to act as a marker of a specific location (e.g., the location of a flow-through passageway between anatomical conduits) subsequent to completion of the interventional procedure.

D. In Situ Modification of the Strut Member(s) and/or Covering to Form or Promote A Desired Flow Path Through the Connector Device FIGS. 7a–7e show a method which may be used for forming opening(s) in the pliable cover 60 of a covered connector device 10 (covered). It will be further appreciated, however, that this method may also be used to effect in situ deformation or separation of adjacent strut members 14a, 14b, 14a (crv), 14b (crv) of any connector device 10, 10', 10 (covered) in order to promote nonturbulant, laminar flow of body fluid (e.g., blood) between those strut members 14a, 14b, 14a (crv), 14b(crv).

Figure 7D:
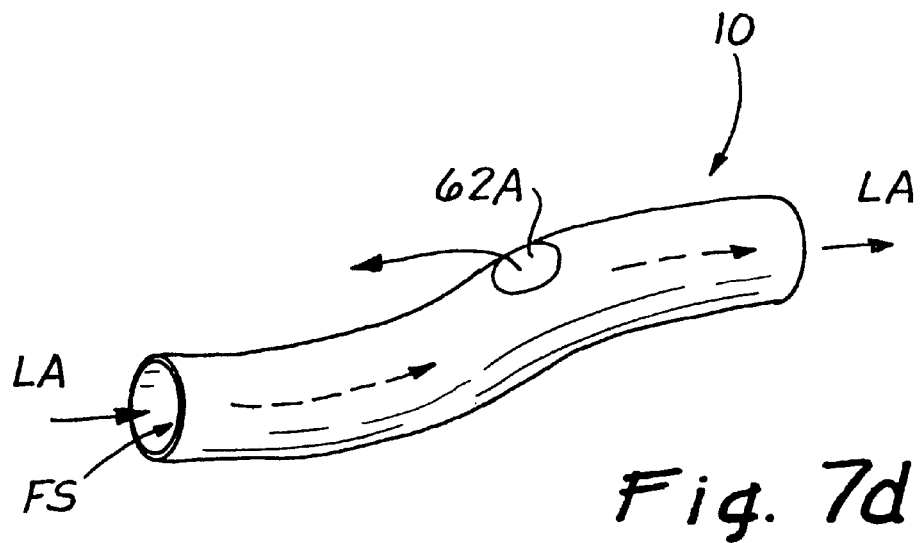
Figure 7E:
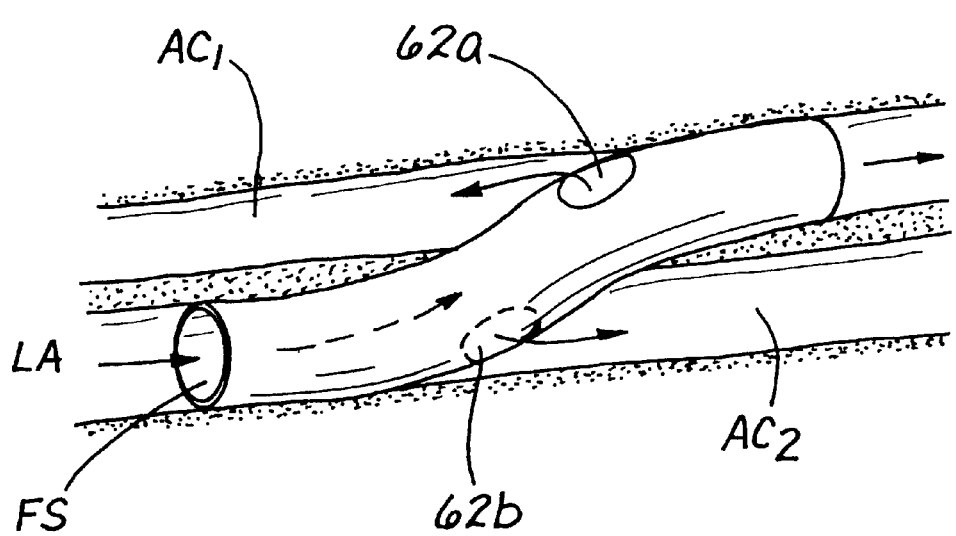

Referring to FIG. 7a, after the connector device 10 (covered) has been implanted in the desired first and second anatomical conduits AC1, AC2, a separate catheter 66 having a cover-puncturing distal tip 67 and a balloon 68 may be advanced through the covering 60 at a desired location (see FIG. 7b) and the balloon 68 may then be inflated to form a desired flow-through opening 62a, 62b in the covering 60 of the connector device 10 (covered). It is to be appreciated that, although FIGS. 7a–7e show a procedure for the in situ formation of flow-through openings 62a, 62b in the covering 60, essentially the same procedure using the catheter 66 (without the puncturing distal tip 67) and its balloon 68 may be used to accomplish in situ bending or deformation of the strut members 14, 14a, 14b, 14a(crv), 14b(crv) of any covered connector device 10 (covered) or non-covered connector device 10, 10' of the present invention, for the purpose of improving flow of body fluid, or improving the stability with which the device 10, 10', 10(covered) is implanted. For example, FIG. 7a illustrates a balloon in phantom having a curvilinear configuration when inflated for deforming the device 10 to a similar post-expansion configuration.

E. Use of the Connector Devices to Exert Traction Upon or Cause Deformation of Surrounding Tissue In some applications of the invention, it may be preferable for the connector device 10, 10', 10 (covered) to exert some traction or force upon surrounding tissues to modify (e.g., remodel, move, reconfigure, compress or otherwise reshape) the surrounding tissues. This aspect of the invention may be particularly useable to minimize the sharpness of corners or bends in an anatomical flow channel or passageway so as to minimize turbulence and/or promote laminar flow through the channel or passageway. In some instances, the desired traction force may be created by implanting two (2) of the connector devices 10, 10', 10 (covered) in opposite orientations, as described more fully in the examples provided herebelow.

In other applications where the un-scaffolded channels or passageways have been formed at the desired angle (e.g., a non-perpendicular angle relative to the longitudinal axis of one of the anatomical conduits), and the curved shape of the connector device(s) 10, 10' and/or the placement of the connector devices 10, 10' in opposite orientations, may be utilized as a means of minimizing the amount of traction upon, or the deformation of, the surrounding tissue.

i. A Method Wherein a Single Delivery Catheter is Used to Implant Two Connector Devices, in Opposite Orientations FIGS. 8a–8e show an example of an approach wherein a single delivery catheter 48 is used to deliver and implant two (2) connector devices 10 in opposite orientations, as shown.

In addition to 1.) holding the adjacent anatomical conduits $AC_1$, $AC_2$ in desired positions relative to each other and ii.) maintaining the patency of the openings $OP_1$, $OP_2$ in the anatomical conduits $AC_1$, $AC_2$ and any intervening tissue positioned therebetween, the connector devices 10, 10' of the present invention may additionally create a desired traction force upon the openings $OP_1$, $OP_2$ and any surrounding or adjacent tissue, to effect a desired deformation or shaping of the flow passageways created between the anatomical conduits $AC_1$, $AC_2$. Such deformation or shaping of the flow passageways may serve to minimize turbulence of the body fluid (e.g. blood) as it flows through the in situ bypass conduit created by a segment of the second anatomical conduit $AC_1$, $AC_2$.

Figure 8A:
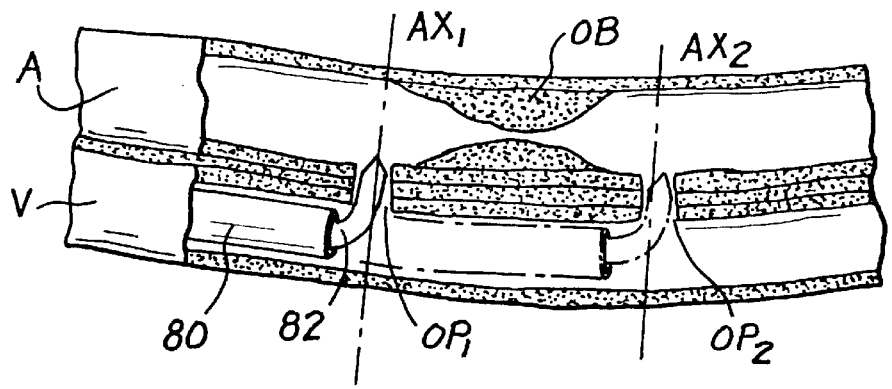
FIGS. 8a–8e are step-wise schematic showings of the performance of one transluminal procedure to bypass of an arterial obstruction using a segment of an adjacent vein as an in situ bypass conduit, and wherein the connector devices of the present invention are implanted in opposing orientations to facilitate smooth, laminar blood flow through the vein segment.
Figure 9A:
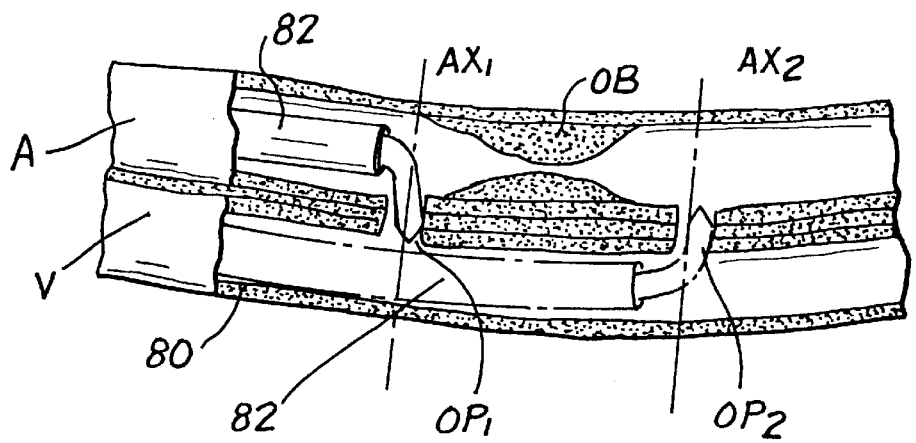
FIGS. 9a–9e are step-wise schematic showings of the performance of another transluminal procedure to bypass of an arterial obstruction using a segment of an adjacent vein as an in situ bypass conduit, and wherein the connector devices of the present invention are implanted in opposing orientations to facilitate smooth, laminar blood flow through the vein segment.

FIG. 8a shows the use of a passageway forming catheter 80 which has been advanced into a vein V and which has a tissue penetrating element 82 extendable laterally therefrom, to form two (2) interstitial blood flow passageways or openings $OP_1$, $OP_2$ between the vein V and an adjacent artery A, for the purpose of bypassing an obstruction OB in the artery A in accordance with the transluminal, in situ bypass method described in copending U.S. patent application Ser. Nos. 08/730,327 and 08/730,496. As shown, the axes $AX_1$, $AX_2$ of the interstitial blood flow passageways or openings $OP_1$, $OP_2$ are initially parallel or substantially parallel to each other, at varying distances. It will be appreciated that the same openings $OP_1$, $OP_2$ could be formed by passing the passageway forming catheter 82 through the artery A (if the obstruction is of a type which will permit such catheter 82 to be passed therethrough) or by placing a first passageway forming catheter 82 in the artery A and a second passageway forming catheter 82 in the vein V as shown in FIG. 9a described herebelow.

After these bloodflow passageways or openings $OP_1$, $OP_2$ have been formed, it may be desired to cause such interstitial blood flow passageways or openings $OP_1$, $OP_2$ to become nonparallel (e.g., to angle inwardly toward one another, in order to promote laminar, nonturbulent blood flow through the segment of the vein V being used as the bypass conduit). To facilitate such alteration or angular disposition of the blood flow passageways or openings $OP_1$, $OP_2$, two (2) connector devices 10 of the present invention will be implanted in opposite orientations, so as to exert traction upon the surrounding tissues and to cause such modification of the openings or passageways $OP_1$, $OP_2$, as illustrated in FIGS. 8b–8e.

Figure 8B:
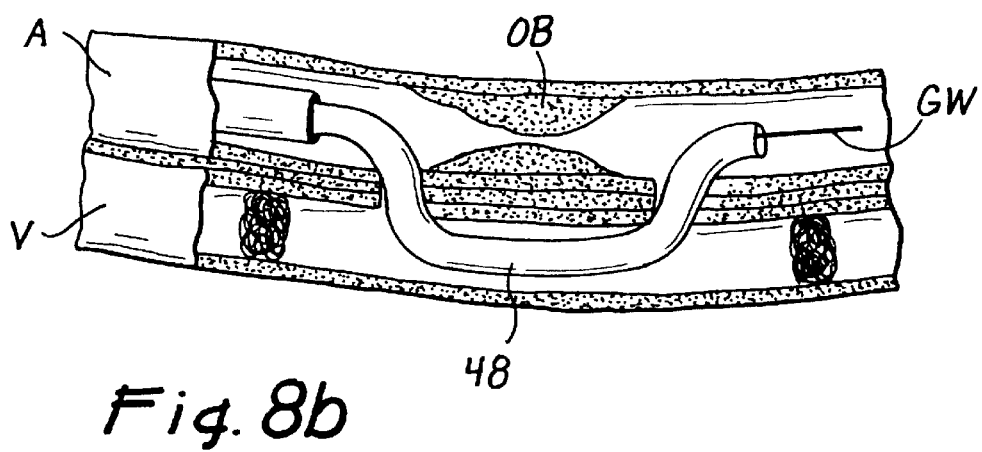

Initially, as shown in FIG. 8b, the connector device delivery catheter 48 is advanced over a guidewire GW from the artery A, through the first blood flow passageway or opening $OP_1$, through the bypass segment of the vein V, back through the second blood flow passageway or opening $OP_2$, and into the artery A distal to the obstruction OB.

Figure 8C:
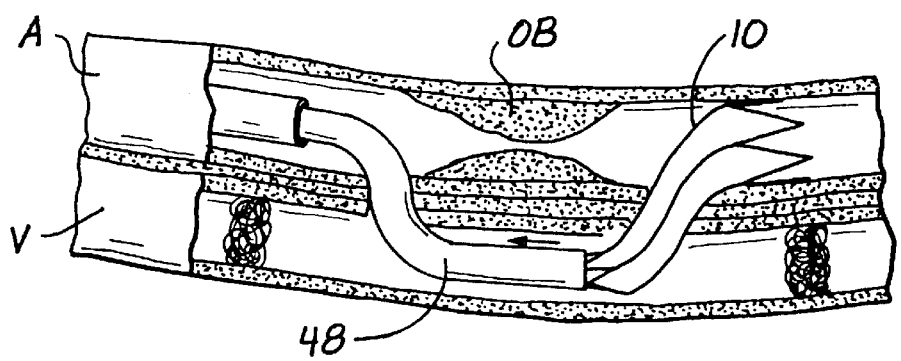

Thereafter, as shown in FIG. 8c, the delivery catheter 48 is slowly withdrawn through the second blood flow passageway or opening $OP_2$ while the distal connector device 10 is implanted within the second blood flow passageway or opening $OP_2$ in the orientation shown in FIG. 8c.

Figure 8D:
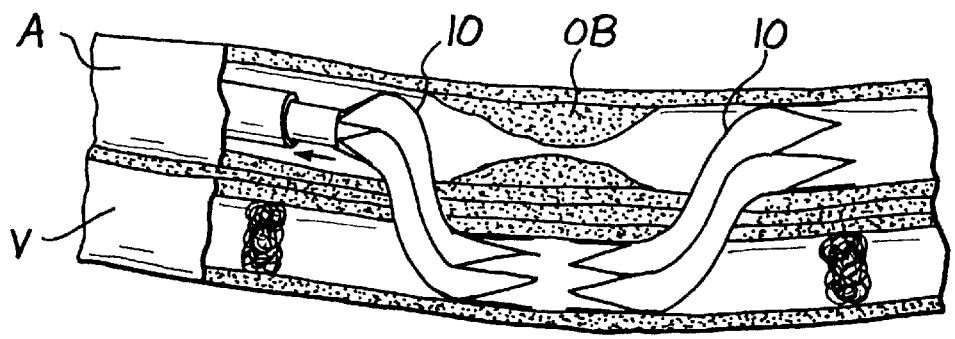

Thereafter, as shown in FIG. 8d, the delivery catheter 48 is further withdrawn through the first blood flow passageway or opening $OP_1$, while the proximal connector device 10 is implanted in the first blood flow passageway or opening $OP_1$ in the opposite orientation shown in FIG. 8d.

Figure 8E:
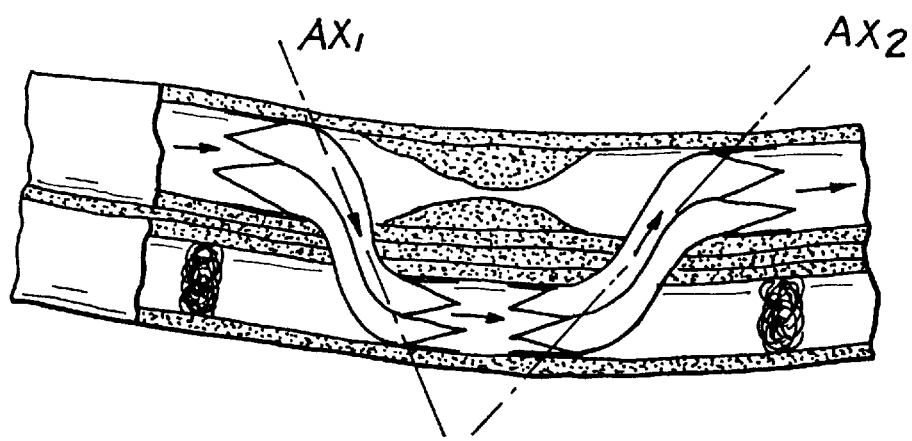

Such implantation of the two connector devices 10 in opposing orientation causes traction to be exerted on the surrounding tissue and results in angulation of the blood flow passageways or openings $OP_1$, $OP_2$ such that the axes $AX_1$, $AX_2$ are no longer substantially parallel to each other, but rather are angled toward each other as shown in FIG. 8e, thereby lessening the potential for disruption or turbulence of blood as it flows through the blood flow passageways or openings $OP_1$, $OP_2$ in the manner indicated by the arrows on FIG. 8e.

ii. Methods Wherein Two Delivery Catheters are Used to Implant Two Connector Devices, in Opposite Orientations FIGS. 9a–9e and 10a–10j show two (2) examples of alternative approaches which may be used to implant two (2) of the connector devices 10 in opposing directions, as was accomplished in the procedure shown in FIGS. 8a–8e described hereabove. In these alternative approaches two (2) delivery catheters are used to deliver and implant the two (2) connector devices 10, as shown.

The Method Shown in FIGS. 9a–9e

FIG. 9a shows the use of a passageway forming catheter 80 which has been advanced into a vein V and which has a tissue penetrating element 82 extendable laterally therefrom, to form two (2) interstitial blood flow passageways or openings $OP_1$, $OP_2$ between the vein V and an adjacent artery A, for the purpose of bypassing an obstruction OB in the artery A in accordance with the transluminal, in situ bypass method described in copending U.S. patent application Ser. Nos. 08/730,327 and 08/730,496. As shown, the axes $AX_1$, $AX_2$ of the interstitial blood flow passageways or openings $OP_1$, $OP_2$ are initially parallel or substantially parallel to each other.

In this particular application of the technology, it is desired to cause the interstitial blood flow passageways or openings $OP_1$, $OP_2$ to become nonparallel and to angle inwardly toward one another, in order to promote laminar, non-turbulent blood flow through the segment of the vein V being used as the bypass conduit. To facilitate such non-parallelism or angular disposition of the blood flow passageways or openings $OP_1$, $OP_2$ two (2) connector devices 10 of the present invention will be inplanted in opposite orientations, as shown in FIGS. 9b–9e.

Figure 9B:
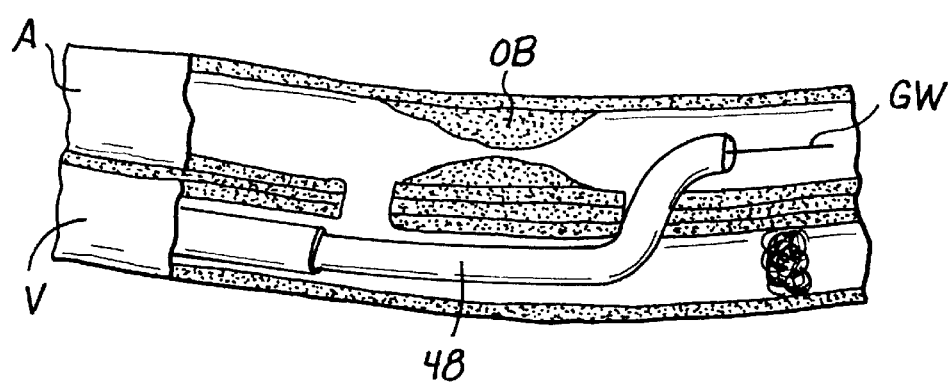

Initially, as shown in FIG. 9b, a first connector device delivery catheter 48a is advanced over a guidewire GW into the vein V, and is used to place a connector device 10 within the second blood flow passageway or opening $OP_2$, between the artery A and vein V, distal to the obstruction OB.

Figure 9C:
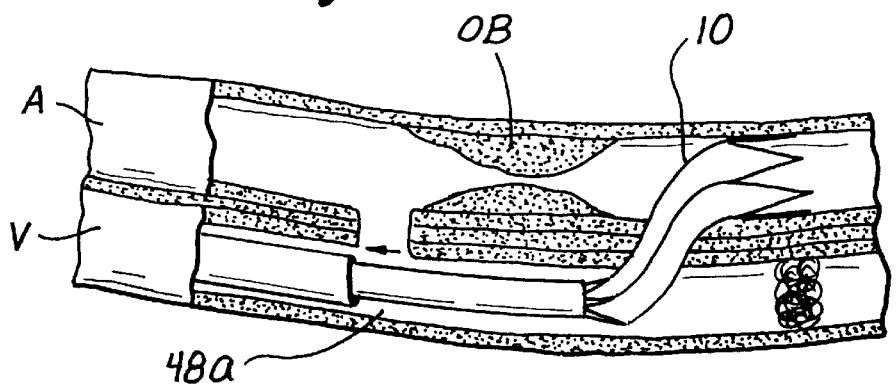
Figure 9D:
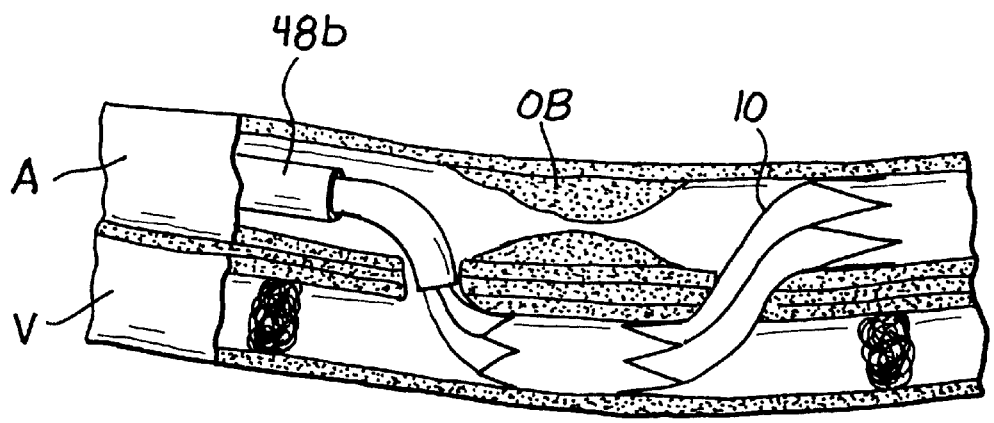

Thereafter, as shown in FIG. 9c, a second delivery catheter 48b is used to place a connector device 10 within the first blood flow passageway or opening OP2, in the opposite orientation shown in FIG. 8d.

Figure 9E:
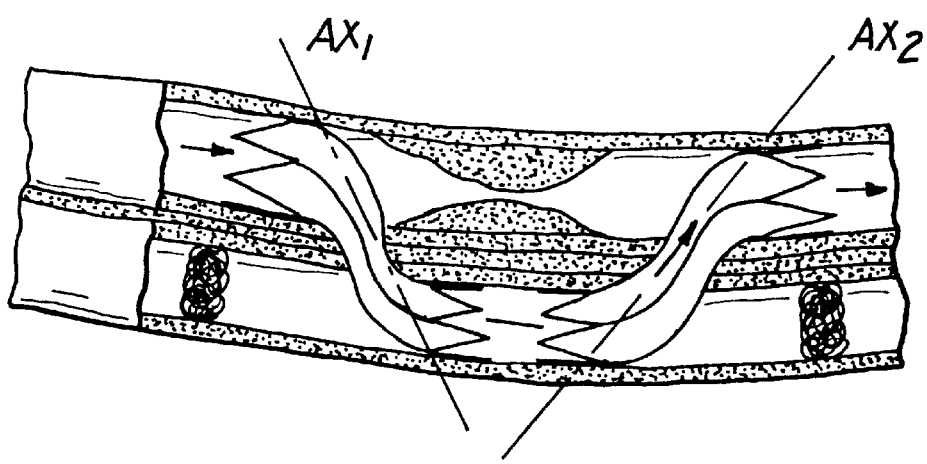

Such implantation of the two connector devices 10 in opposing orientation causes traction to be exerted on the surrounding tissue and results in angulation of the blood flow passageways or openings $OP_1$, $OP_2$ such that the axes $AX_1$, $AX_2$ are no longer substantially parallel to each other, but rather are angled toward each other as shown in FIG. 9e, thereby lessening the potential for disruption or turbulence of blood as it flows through the blood flow passageways or openings $OP_1$, $OP_2$ in the manner indicated by the arrows on FIG. 9e.

The Method Shown in FIGS. 10a–10i

Figure 10A:
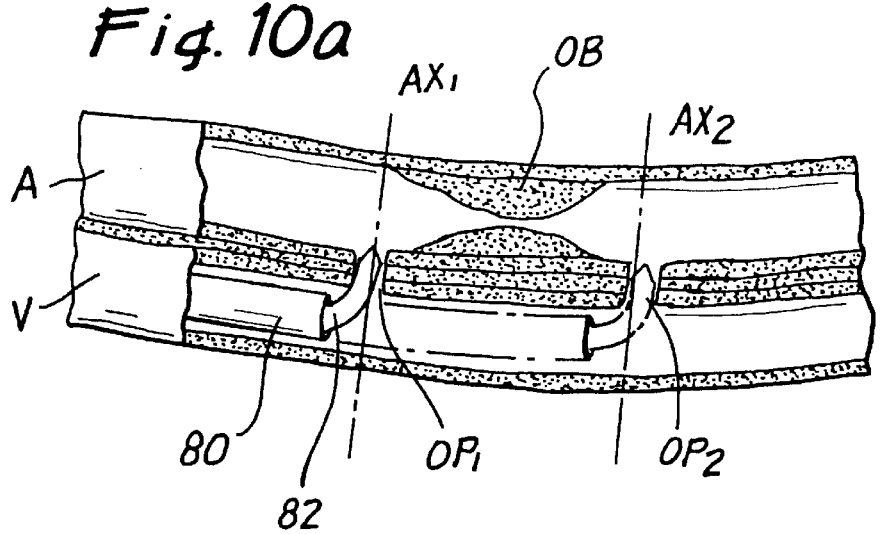
FIGS. 10a–10j are step-wise schematic showings of the performance of another transluminal procedure to bypass of an arterial obstruction using a segment of an adjacent vein as an in situ bypass conduit, and wherein the connector devices of the present invention are implanted in opposing orientations to facilitate smooth, laminar blood flow through the vein segment.

FIG. 10a shows the use of a passageway forming catheter 80 which has been advanced into a vein V and which has a tissue penetrating element 82 extendable laterally therefrom, to form two (2) interstitial blood flow passageways or openings $OP_1$, $OP_2$ between the vein V and an adjacent artery A, for the purpose of bypassing an obstruction OB in the artery A in accordance with the transluminal, in situ bypass method described in copending U.S. patent application Ser. Nos. 08/730,327 and 08/730,496. As shown, the axes $AX_1$, $AX_2$ of the interstitial blood flow passageways or openings $OP_1$, $OP_2$ are initially parallel or substantially parallel to each other.

As in the above-described examples of FIGS. 8a–8e and 9a–9e, it is desired to cause the interstitial blood flow passageways or openings $OP_1$, $OP_2$ to become nonparallel and to angle inwardly toward one another, in order to promote laminar, non-turbulent blood flow through the segment of the vein V being used as the bypass conduit. To facilitate such non-parallelism or angular disposition of the blood flow passageways or openings $OP_1$, $OP_2$ two (2) connector devices 10 of the present invention will again be implanted in opposite orientations.

Figure 10B:
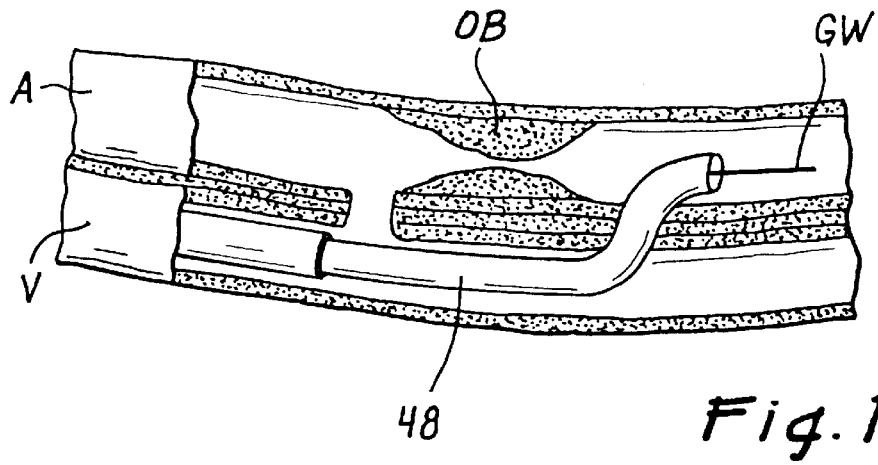
Figure 10C:
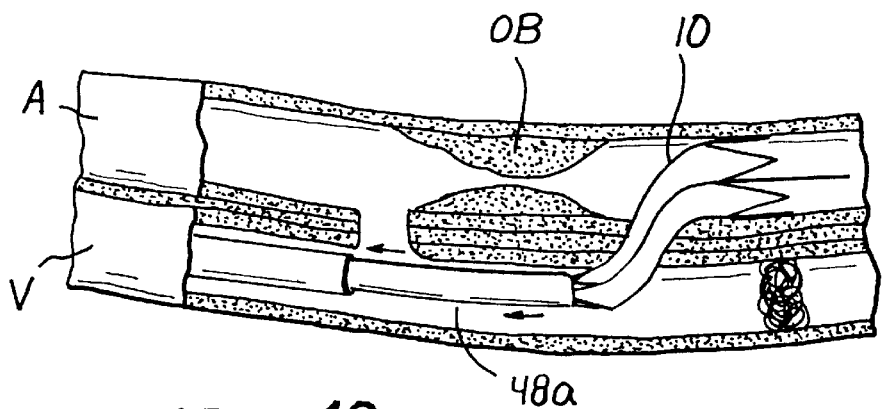
Figure 10D:
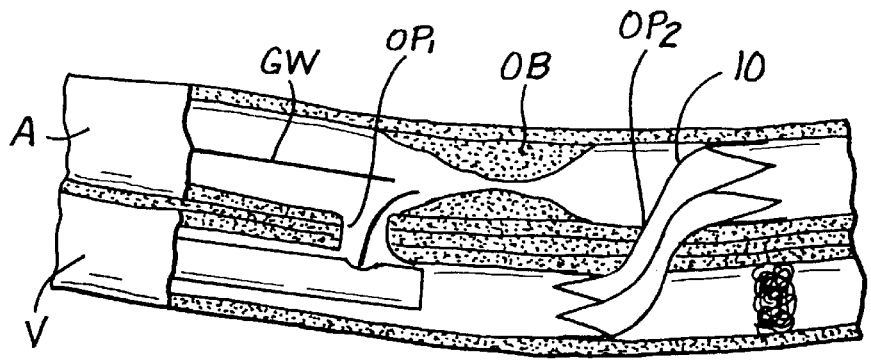

Initially, as shown in FIGS. 10b and 10c, a first connector device delivery catheter 48a is advanced over a guidewire GW into the vein V, and is used to place a connector device 10 within the second blood flow passageway or opening $OP_2$, between the artery A and vein V, distal to the obstruction OB.

Thereafter, as shown in FIGS. 10d–10g, a guidewire GW is advanced into the atrery A such that the distal end of the guidewire GW is located next to the proximal passageway or opening $OP_1$. A guidewire captureing catheter 100 having a guidewire capturing apparatus 102 advanceable therefrom, is advanced into the vein V adjacent to the first passageway or opening $OP_1$, and the guidewire capturing apparatus 102 is advanced through the first passageway or opening $OP_1$ and is used to capture the guidewire GW at a location near its distal end, as shown. Thereafter, the guidewire capturing apparatus 102 and/or catheter 100 is/are manipulated and/or retracted to pull the distal end of the guidewire GW through the first passageway or opening $OP_1$, such that the distal end of the guidewire GW is positioned within the vein V, distal to the first passageway or opening $OP_1$, as shown. The guidewire capturing apparatus used in this step of the procedure may be any type of member or apparatus which is useable for this purpose, including but not limited to intraluminal snares and graspers of the type well known in the field of interventional radiology. Examples of commercially available snares or graspers which may be useable or modifiable for this application include the Cordis BI PAL formable/torquable disposable biopsy forceps(Cordis -----, Miami, Fla.); the BYCEP P.C. pre-curved biopsy forcep (Mansfield-Boston Scientific Corporation, Watertown, Mass.); the Intravascular Snare (Cook, Inc., Bloomington, Ind.); and the Microvena Retrieval Snare (Microvena Corporation, White Bear Lake, Minn.).

Figure 10E:
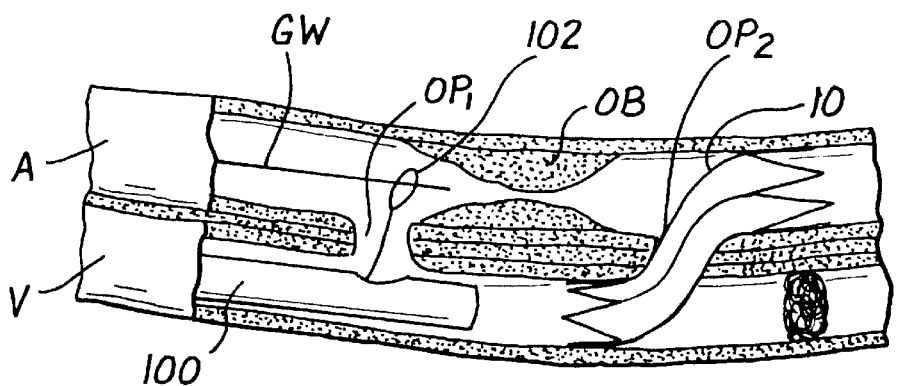
Figure 10F:
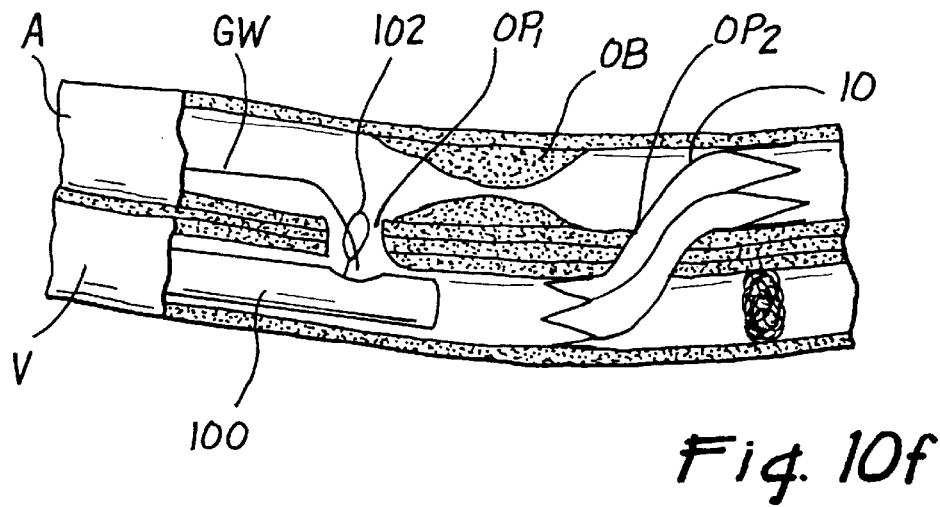
Figure 10G:
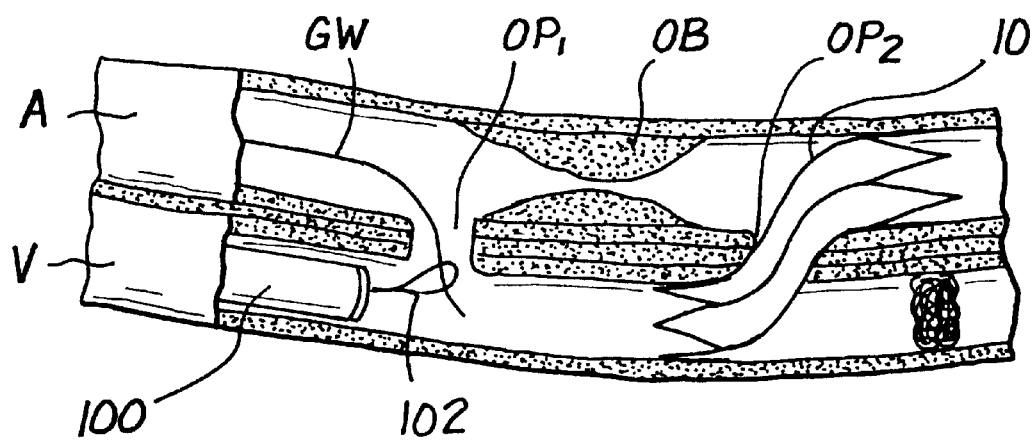
Figure 10H:
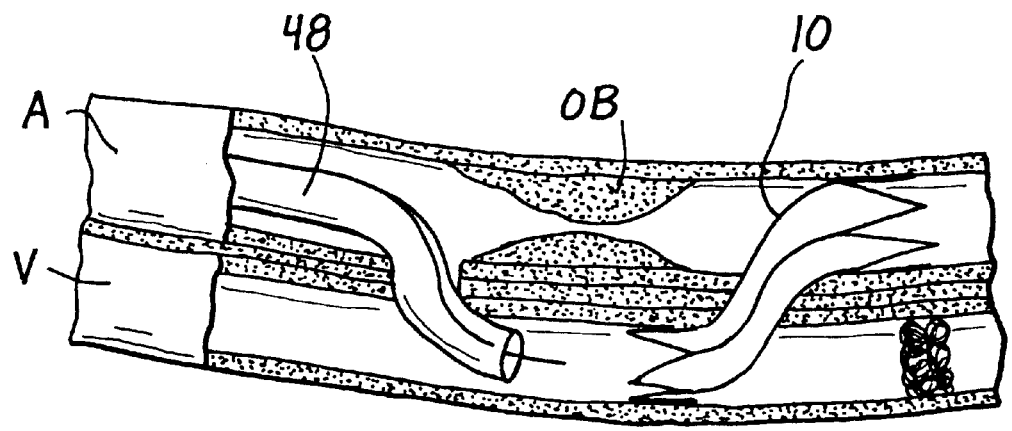
Figure 10I:
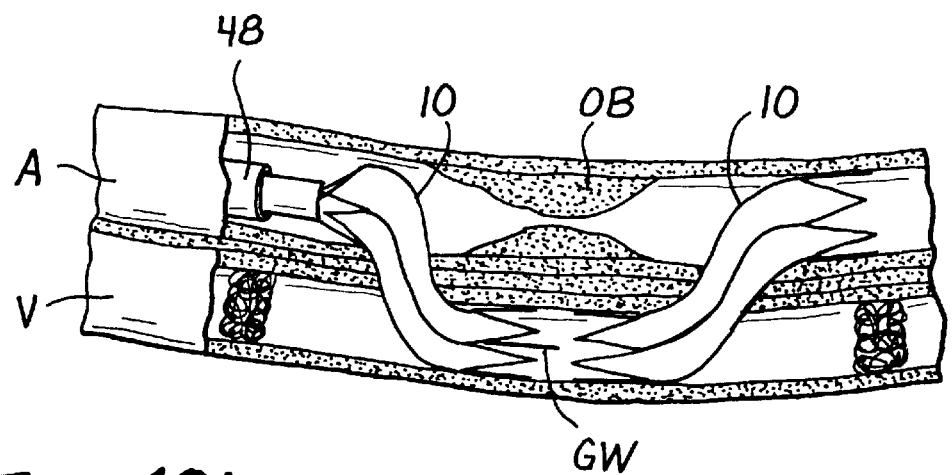
Figure 10J:
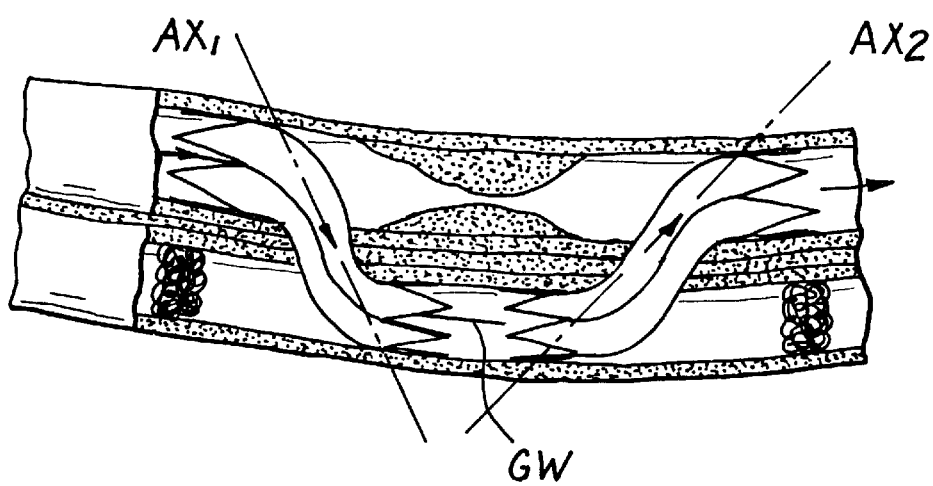

Thereafter, as shown in FIG. 10h–10j, a second delivery catheter 48b is advanced through the artery A, over the guidewire GW, and through the first passageway or opening $OP_1$ and is used to place a second connector device 10 within the first blood flow passageway or opening $OP_1$, in the opposite orientation shown in FIG. 8d.

Such implantation of the two connector devices 10 in opposing orientation causes traction to be exerted on the surrounding tissue and results in angulation of the blood flow passageways or openings $OP_1$, $OP_2$ such that the axes $AX_1$, $AX_2$ are no longer substantially parallel to each other, but rather are angled toward each other as shown in FIG. 10e, thereby lessening the potential for disruption or turbulence of blood as it flows through the blood flow passageways or openings $OP_1$, $OP_2$ in the manner indicated by the arrows on FIG. 10e.

F. Use of a Partially Covered Connector Device to Block Outflow through Side Branches which Emanate from the Anatomical Conduit(s)

FIGS. 11a–11e show an example of a procedure wherein a single, partially covered, connector device 10 (covered) is used to simultaneously a) maintain flow through first and second bloodflow passageways or openings $OP_1$, $OP_2$ and b) block the outflow of blood through venous side branches SB which emanate from the segment of vein V being used as an in situ bypass conduit.

Figure 11A:
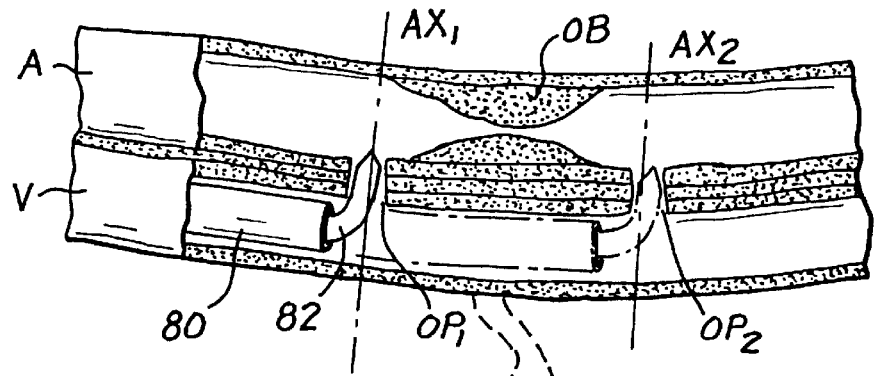
FIGS. 11a–11e are step-wise schematic showings of the performance of another transluminal procedure to bypass of an arterial obstruction using a segment of an adjacent vein as an in situ bypass conduit, and wherein a single connector device of the present invention, which incorporates a partial covering thereon, is implanted such that a) its proximal and distal annular members are disposed in a single artery at locations upstream and downstream of an obstruction, b) its strut members extend through a segment of an adjacent vein, and c) its covering serves to block to outflow of blood into venous side branches which emanate from the segment of vein.

Initially, as shown in FIG. 11a, a passageway forming catheter 80 is utilized to form first and second bloodflow passageways or openings $OP_1$, $OP_2$ between an artery A and vein V. As discussed hereabove with reference to FIGS. 8a–8d, 9a–9e, and 10a–10j, the passageway forming catheter 80 may alternatively be passed into the artery A or into both the artery A and vein V to create these bloodflow passageways or openings $OP_1$, $OP_2$ having axes $AX_1$, $AX_2$ which are substantially parallel to each other, as shown in FIG. 11a.

Figure 11B:
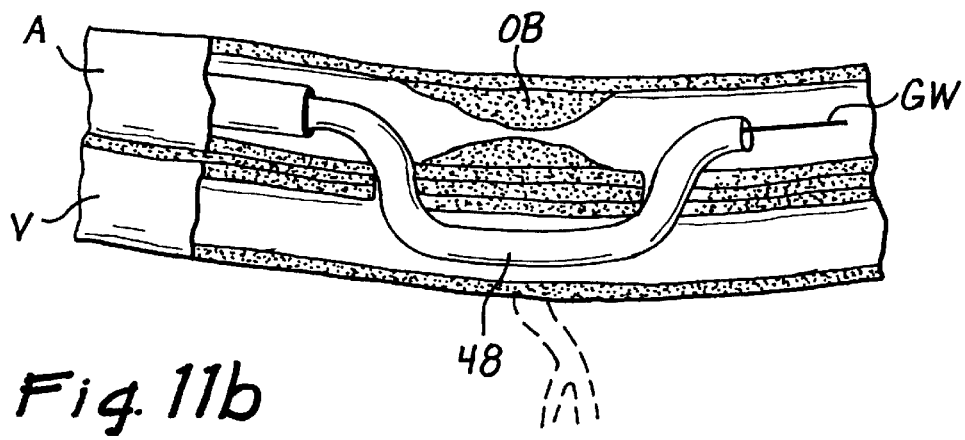

Thereafter, as illustrated in FIG. 11b a guidewire GW is advanced through the artery A, through the first passageway or opening $OP_1$, through the adjacent segment of the vein V, and through the second passageway or opening $OP_2$, such that the distal end of the guidewire GW is located in the artery A downstream of the obstruction OB. A connector device delivery catheter 48 having the a single, partially covered, connector device 10 (covered) loaded therein is then advanced over the guidewire until the distal end of the delivery catheter 48 is also in the artery A, downstream of the obstruction OB, as shown.

Figure 11C:
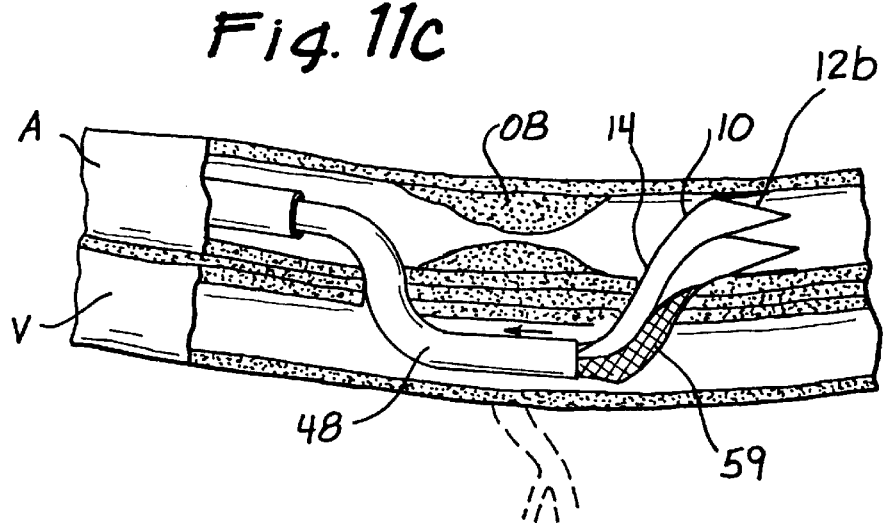
Figure 11D:
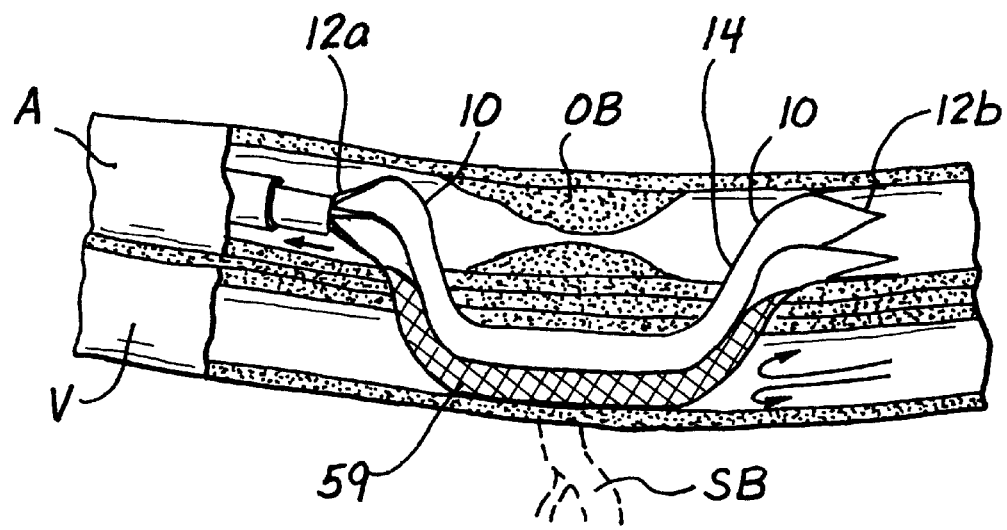
Figure 11E:
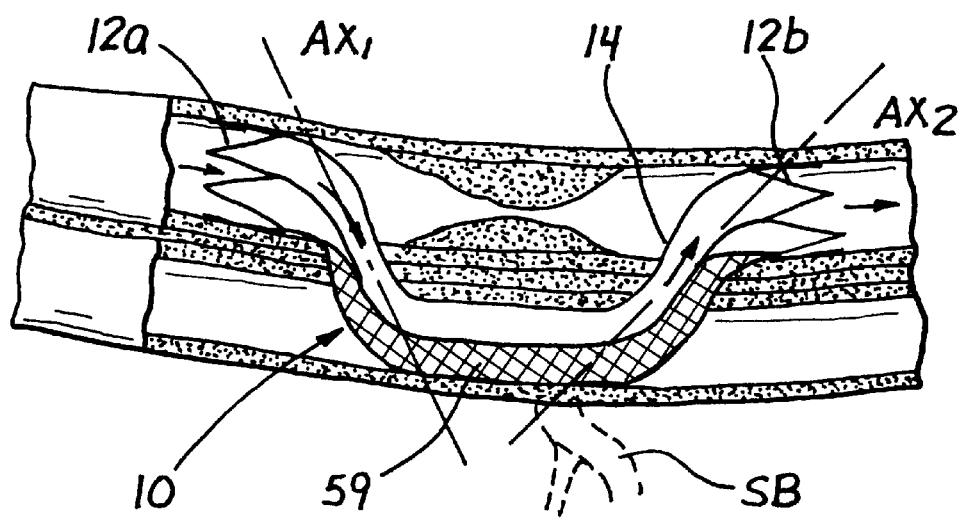

Thereafter, as shown in FIGS. 11c–11d, the connector device 10 (covered) is advanced out of the distal end of the delivery catheter 48 as the delivery catheter is slowly retracted. This results in the single connector device 10 (covered) being implanted such that its distal annular member 12 b is positioned within the artery A downstream of the obstruction, its proximal annular member 12a is positioned within the artery A upstream of the obstruction, and its strut members 14 extend through the first and second passageways or openings $OP_1$, $OP_2$, and through the segment of vein V being used as the in situ bypass conduit.

As shown in FIG. 11e, the partial covering 59 disposed on one side of the strut members 14 of the connector device 10 (covered) is positioned in contact with the adjacent wall of the vein V so as to prevent blood from flowing into any venous side branch SB which emanates from that portion of the vein V. Additionally, the partial covering 59 blocks the flow of venous return through the portion of the vein V being used as the in situ bypass conduit. Also, as shown, this disposition of a single, partially covered, two-annular-member connector device 10 (covered) exerts traction upon the surrounding tissue so as to cause the axes $AX_1$, ,$AX_2$ of the passageways or openings $OP_1$, $OP_2$ to angle inwardly such that they are no longer parallel. This serves to minimize turbulence of the blood flowing through this bypass conduit.

G. Implantation of the Connector Devices within Bifurcated Anatomical Conduits

Figure 12:
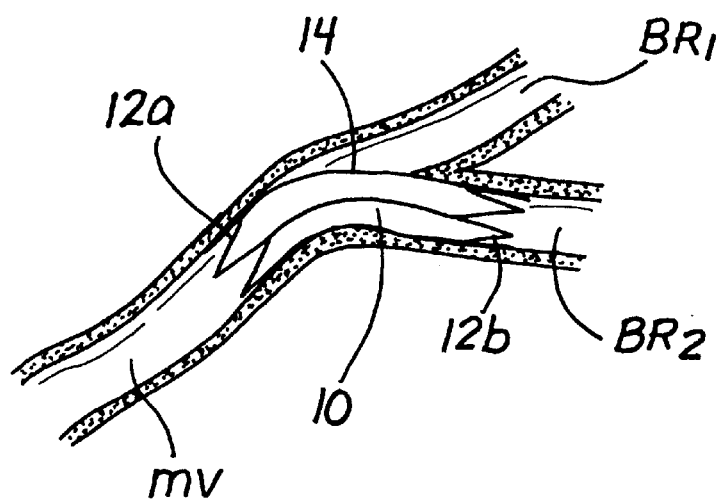
FIG. 12 shows the manner in which body fluid (e.g., blood) may flow between the strut members of certain embodiments of the connector members of the present invention.
Figure 13:
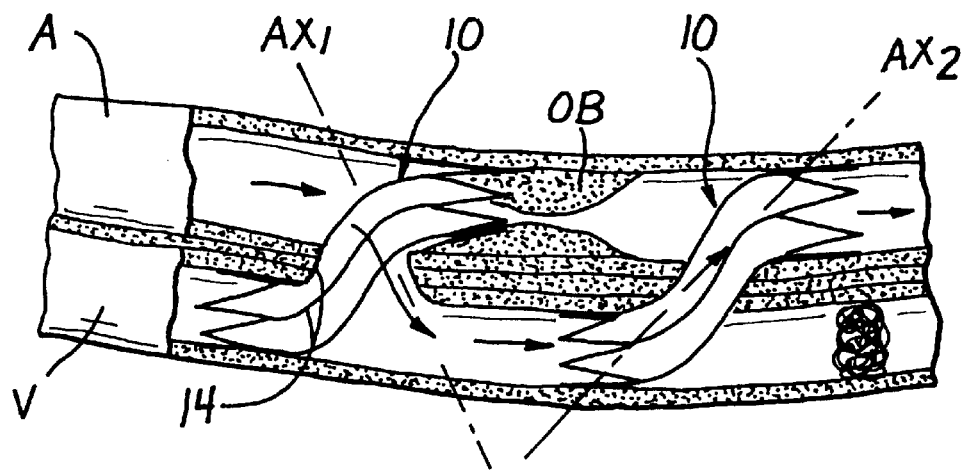
FIG. 13 is a perspective view of a connector device of the present invention implanted within a bifurcated anatomical conduit.
Figure 14:
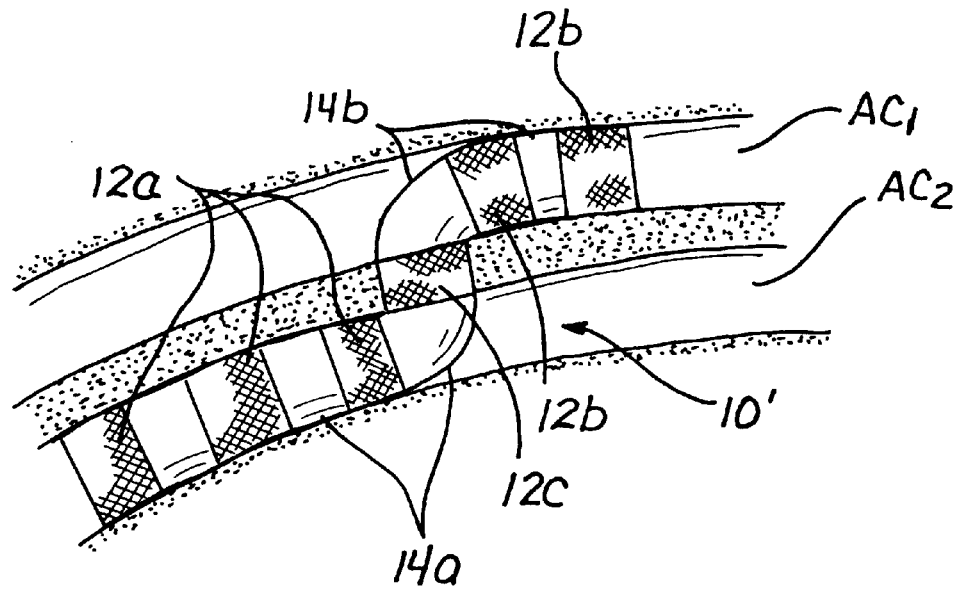
FIG. 14 is a schematic, elevational view of adjacent anatomical conduits having a single passageway formed therebetween and a three-annular-member connector device (which includes more than one proximal annular member and more than one distal annular member) implanted within the passageway such that it extends into both anatomical conduits.

FIG. 12 shows an example of the manner in which a two-annular-member connector device 10 of the present invention may be implanted within a bifurcated vessel. As shown, the main vessel MV bifurcates into a first branch BR1 and a second branch BR2. The connector device 10 is positioned such that its proximal annular member 12a is in the main vessel MV, its distal annular member 12b is in the second branch vessel BR2 and its strut members 14 extend therebetween.

H. Connector Devices Having Additional Annular Members

Figure 15:
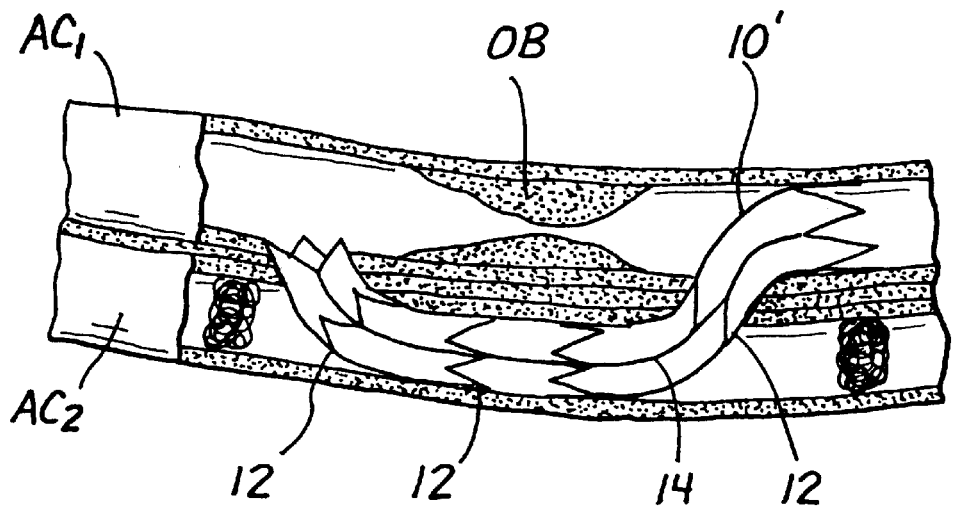
FIG. 15 is a schematic, elevational view of adjacent anatomical conduits having two interstitial passageways formed therebetween and the connector device of FIG. 14 implanted therein such that one end of the device extends into one of the anatomical conduits and the other end of the device is positioned within one of the interstitial passageways.
Figure 16:
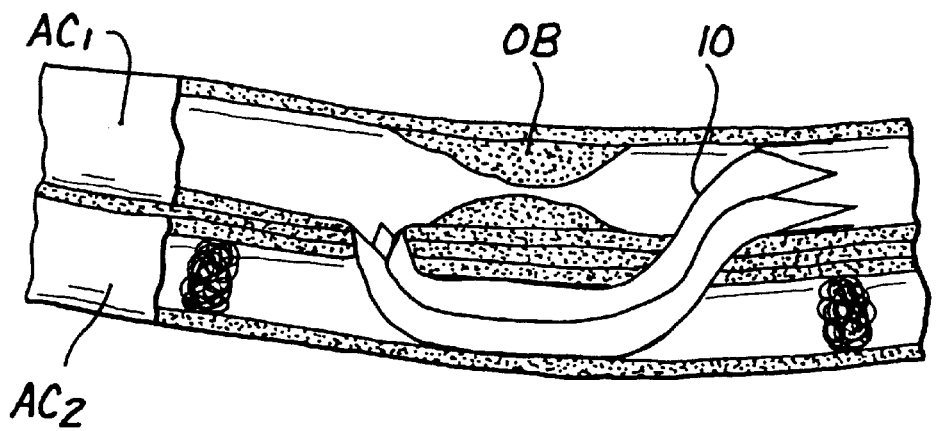
FIG. 16 is a schematic, elevational view of adjacent anatomical conduits having two interstitial passageways formed therebetween and two-annular-member connector device implanted therein such that one end of the device extends into one of the anatomical conduits and the other end of the device is positioned within one of the interstitial passageways.

It will be appreciated that the two-annular-member connector device 10 has at least two annular members 12a, 12b, but may include more. Likewise, the three-annular-member connector device 10' has at least three annular members 12a, 12b, 12c, but may include more. Examples of three-annular-member connector devices which incorporate more that thee annular members 12a, 12b, 12c, are shown in FIGS. 15 and 16. As shown, depending on the positioning of the device 10' following implantation, the additional proximal, distal or medial annular members 12a, 12b, 12c may serve to provide additional scaffolding or support for the anatomical conduits $AC_1$, $AC_2$ or the interstitial passageways formed therebetween.

I. Variable Positioning of the Connector Devices to Accommodate Anatomical Differences and/or to Effect Specialized Therapeutic Applications The connector devices 10, 10', 10 (covered) may be implanted at various locations and/or positions to achieve the desired therapeutic result (e.g., to facilitate flow of body fluid in the desired through a passageway which has been formed between those anatomical conduits. In other applications, as illustrated in FIGS. 15–17, the connector device 10, 10', 10 (covered) may be implanted such that it extends through multiple interstitial passageways, and/or so that it does not extend into specific regions of the anatomical conduits $AC_1$, $AC_2$.

It is to be further understood that the diameters or sizes of the annular members 12a, 12b, 12c of a single device 10, 10', 10(covered) may vary when in their radially expanded states. Such variation in the diameters or sizes of the annular members 12a, 12b, 12c may be utilized to accommodate vessels or passageways of varying size. (e.g., a vein of one diameter and an adjacent artery of another diameter).

Figure 18:
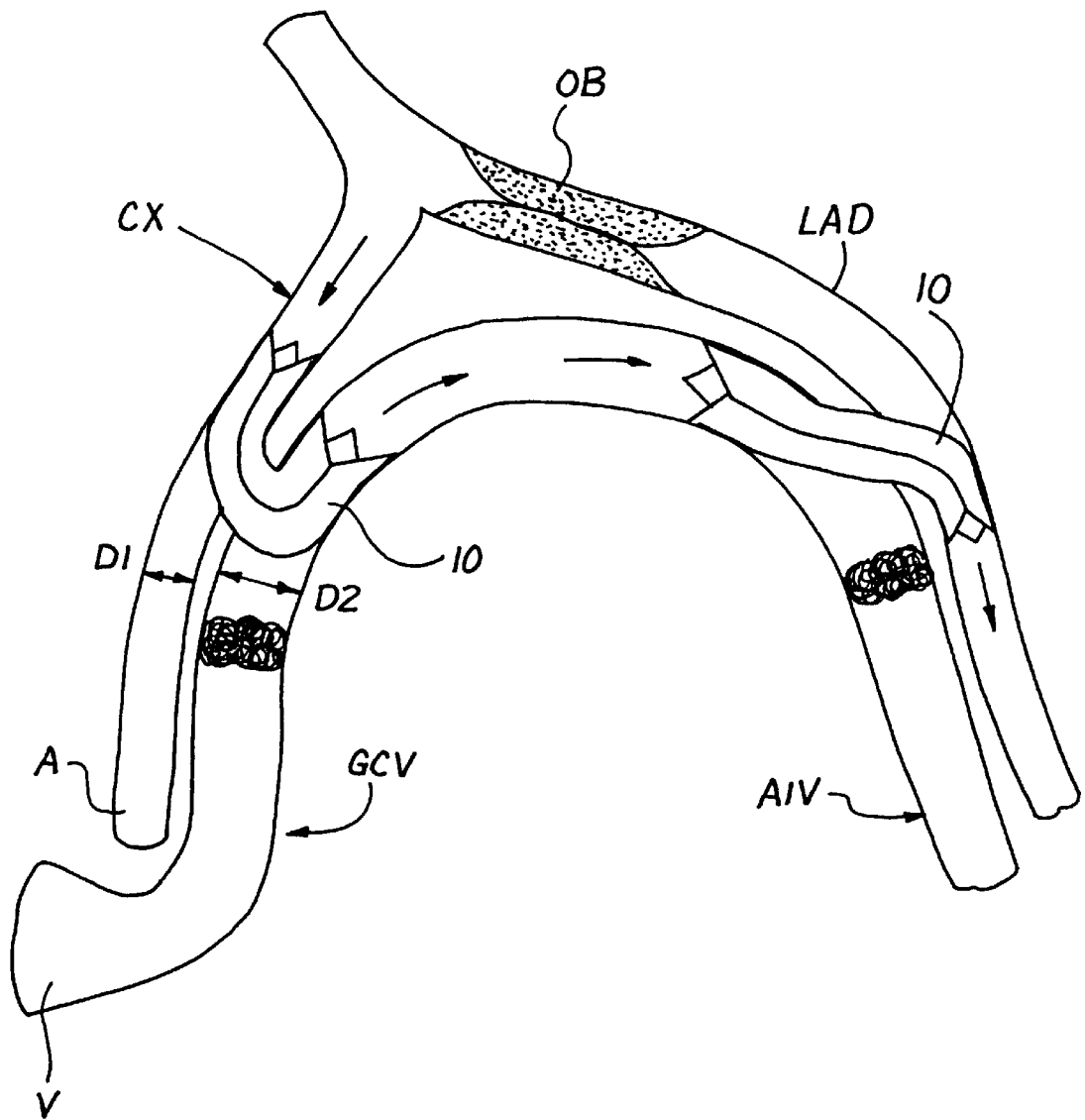
FIG. 18 is a schematic showing of the anatomical "Brouck-Moscheau" having i) a first interstitial passageway formed between the Circumflex coronary artery and the Great Cardiac Vein, ii) a second interstitial passageway formed between the Anterior Interventricular Vein and the Left Anterior Descending coronary artery, and iii) connector devices of the present invention disposed within those first and second interstitial passageways to facilitate coronary revascularization.

J. A Method for Coronary Revascularization within the Triangle of Brouck-Moscheau Using Connector Devices of the Present Invention FIG. 18 is a diagram of a portion of the coronary vasculature known as the Triangle of Brouck-Moscheau. The Triangle of Brouck-Moscheau is defined by the left anterior descending coronary artery LAD, the circumflex coronary artery CIR, the anterior interventricular vein AIV and the great cardiac vein, GCV, as shown. In the case illustrated in FIG. 18, an obstruction OB, such as a build-up of atherosclerotic plaque, is found in the proximal portion of the left anterior descending artery LAD. A revascularization procedure has been carried out to bypass such obstruction OB in the left anterior descending artery LAD by forming a first interstitial passageway or opening $OP_1$ between the circumflex artery CX and the Great Cardiac Vein GCV, and a second interstitial passageway or opening $OP_2$ between the Anterior Interventricular Vein AIV and the Left Anterior Descending artery LAD, downstream of the obstruction OB. A first lumen blocking member 50a has been placed within the great cardiac vein GCV, proximal to the first passageway or opening $OP_1$ and a second lumen blocking member 50b has been placed within the anterior interventricular vein AIV, distal to the second passageway or opening $OP_2$ such that arterial blood from the circumflex artery CIR will flow through the first blood flow passageway 10a, through the great cardiac vein GCV, through the anterior interventricular vein AIV and into the left anterior descending artery LAD, downstream of the obstruction. One connector device of the present invention 10 has been implanted, in a generally U-shaped configuration, within the first passageway or opening $OP_1$ and another connector device 10 has been implanted, in a generally serpentine or "S" shaped configuration within in the second interstitial passageway or opening $OP_2$. These connector devices serve to maintain patency and alignment of the passageways or openings $OP_1$, $OP_2$ such that blood will continue to freely flow through the adjacent segment of the Great Cardiac Vein GCV/Anterior Interventricular Vein AIV, thereby bypassing the obstruction OB and providing restored arterial bloodflow to the portion of the Left Anterior Descending artery downstream of the obstruction.

Figure 17:
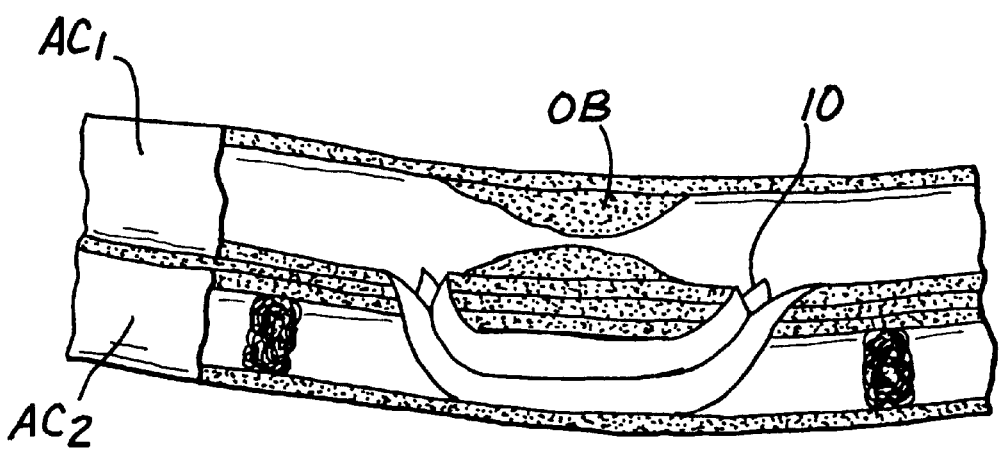
FIG. 17 is a schematic, elevational view of adjacent anatomical conduits having two interstitial passageways formed therebetween and the two-annular-member connector device of FIG. 16 implanted therewithin such that one end of the device terminates in one of the interstitial passageways and the other end of the device terminates within the other interstitial passageway.

The connector device 10 positioned in the first passageway or opening $OP_1$ may be preformed to the desired "U" and expelled from a delivery catheter which has been advanced into the Great Cardiac Vein GCV and at least partially through the first passageway of opening $OP_1$, such that the connector 10 will resiliently assume the "U" configuration shown in FIG. 17. The other connector device positioned within the second passageway or opening $OP_2$ may be preformed to a serpentine or "S" shaped configuration and may be implanted by the technique shown in FIGS. 5a–5c and described in detail hereabove.

It will be appreciated that the invention has been described hereabove and shown in the drawings with reference to certain presently preferred embodiments or examples only and no attempt has been made to exhaustively describe all possible embodiments and examples of the invention. Indeed, those skilled in the relevant art will understand that numerous modifications may be made to the above-described embodiments and examples without departing from the intended spirit and scope of the invention, and it is intended that all such modifications be included within the scope of the following claims.

What is claimed is:

1. A device for facilitating fluid flow between a first opening formed in a first anatomical conduit and a second opening formed in a second anatomical conduit, said device comprising:

at least one proximal annular member and at least one distal annular member, each of said annular members having a radially compact configuration and a radially expanded configuration, the proximal annular member being sized to expand into contact with the first anatomical conduit, and the distal annular member being sized to expand into contact with the second anatomical conduit;

at least one curvilinear strut member connected to and extending between said proximal and distal annular members, said at least one strut member having a pre-expansion configuration and a post-expansion configuration, wherein outer ones of said strut members have a longer radius of curvature than inner ones of said strut members when the device is in its post-expansion configuration, and wherein said outer ones of said strut members are longer in length than said inner ones of said strut members, said outer ones of said strut members having at least one curvilinear wave formed therein while the device is in its pre-expansion configuration;

said device being initially transluminally deliverable with its annular members in their radially collapsed configurations and said at least one strut member is in its pre-expansion configuration, and wherein the at least one curvilinear post-expansion strut member is configured to maintain a patent curvilinear fluid flow path between the first and second conduits and through the device; and, said device being thereafter implantable with its annular members are in their radially expanded configurations and said at least one strut member is in its post-expansion configuration.

2. The device of claim 1 wherein said at least one strut member comprises a plurality of strut members.

3. The device of claim 1 having 4 to 8 strut members.

4. The device of claim 1 wherein said strut members are spaced apart from each other and disposed about a central axis when the device is in its implanted state, such that a hollow channel is defined within said strut members.

5. The device of claim 1 wherein said at least one strut member is formed of resilient material such that it remains in its pre-expansion configuration when radially constrained, but will assume its post-expansion configuration when radially unconstrained.

6. The device of claim 5 wherein said resilient material is selected from the group of resilient materials consisting of:
spring metal;
a resilient polymer; and,
a shape memory alloy.

7. The device of claim 1 wherein said at least one strut member(s) is/are formed of malleable material.

8. The device of claim 7 wherein said malleable material is selected from the group of malleable materials consisting of:
plastically deformable metal; and,
plastically deformable polymer.

9. A system comprising:
a device for facilitating fluid flow between a first opening formed in a first anatomical conduit and a second opening formed in a second anatomical conduit, said device comprising:
at least one proximal annular member and at least one distal annular member, each of said annular members having a radially compact configuration and a radially expanded configuration, the proximal annular member being sized to expand into contact with the first anatomical conduit, and the distal annular member being sized to expand into contact with the second anatomical conduit;
at least one curvilinear strut member connected to and extending between said proximal and distal annular members, said at least one strut member having a pre-expansion configuration and a post-expansion configuration, wherein outer ones of said strut members have a longer radius of curvature than inner ones of said strut members when the device is in its post-expansion configuration, and wherein said outer ones of said strut members are longer in length than said inner ones of said strut members, said outer ones of said strut members having at least one curvilinear wave formed therein while the device is in its pre-expansion configuration;
said device being initially transluminally deliverable with its annular members in their radially collapsed configurations and said at least one strut member is in its pre-expansion configuration, and wherein the at least one curvilinear post-expansion strut member is configured to maintain a patent curvilinear fluid flow path between the first and second conduits and through the device; and,
said device being thereafter implantable with its annular members are in their radially expanded configurations and said at least one strut member is in its post-expansion configuration; and
a pressure-exerting member positioned within said device and useable to cause the annular members to radially expand and the at least one strut member to deform from its pre-expansion configuration to its post-expansion configuration.

10. The system of claim 9 wherein said pressure-exerting device is a balloon which has a curved configuration when inflated to deform said strut members to a curvilinear post-expansion configurations.

11. The device of claim 1 wherein said annular members are self-expanding.

12. The device of claim 8 wherein said self-expanding annular members are formed of resilient material and are biased to their radially expanded configurations.

13. The device of claim 12 wherein said resilient material is selected from the group consisting of:
spring metal;
resilient polymer; and,
shape memory alloy.

14. The device of claim 1 wherein said annular members are pressure-expandable.

15. The device of claim 14 wherein said pressure-expandable annular members are formed of malleable material capable of being plastically deformed from their radially compact configurations to their radially expanded configurations.

16. The device of claim 15 wherein said malleable material is selected from the group of malleable materials consisting of:
plastically deformable metal; and
plastically deformable polymer.

17. The device of claim 1 wherein said at least one strut member has first and second ends, said first and second ends being fused to said first and distal annular members.

18. The device of claim 13 wherein said at least one strut member has first and second ends which are connected to said first and distal annular members by flexible connections.

19. The device of claim 10 wherein loops are formed on the first and second ends of said at least one strut member, and portions of said first and distal annular members are captured within said loops, to thereby form said flexible connections between the ends of said at least one strut member and first and distal annular members.

20. The device of claim 1 wherein the curvilinear post-expansion configuration of said at least one strut member is a serpentine configuration.

21. The device of claim 1 wherein the curvilinear post-expansion configuration of said at least one strut member is a generally U shaped configuration.

22. The device of claim 1 further comprising:
a plurality of transverse strut connector members formed between adjacent ones of said strut members.

23. The device of claim 1 further comprising a pliable covering formed on at least a portion of said device.

24. The device of claim 23 wherein said pliable covering is a generally cylindrical covering formed about said device, said cover defining a hollow lumen which extends longitudinally through the device.

25. The device of claim 23 wherein at least one flow-through opening is formed in said pliable covering.

26. A device for facilitating fluid flow between a first opening formed in a first anatomical conduit and a second opening formed in a second anatomical conduit, said device comprising:
at least one proximal annular member and at least one distal annular member, each of said annular members having a radially compact configuration and a radially expanded configuration, the proximal annular member being sized to expand into contact with the first anatomical conduit, and the distal annular member being sized to expand into contact with the second anatomical conduit;
at least one strut member connected to and extending between said proximal and distal annular members, said at least one strut member having a pre-expansion configuration and a post-expansion configuration;
said device being initially transluminally deliverable with its annular members in their radially collapsed configurations and said at least one strut member is in its pre-expansion configuration, wherein the post-expansion configuration of said at least one strut member is curvilinear, and wherein the at least one curvilinear post-expansion strut member is configured to maintain a patent curvilinear fluid flow path between the first and second conduits and through the device;

said device being thereafter implantable with its annular members are in their radially expanded configurations and said at least one strut member is in its post-expansion configuration; and further comprising a pliable covering formed transversely across the device to block flow of body fluid.

27. The device of claim 1 wherein said at least one strut member has a post-expansion configuration which is multicurvate, such that said proximal and distal annular members may be positioned at spaced-apart locations in the same anatomical conduit and said at least one strut member may extend through said first and second openings and through a segment of an adjacent second anatomical conduit.

28. The device of claim 1 wherein at least some of the proximal and distal annular members are of differing size when in their radially expanded configurations.

29. A device for facilitating fluid flow between the lumen of a first anatomical conduit which has a first opening formed therein, and the lumen of a second anatomical conduit which has a second opening formed therein, said device comprising:

at least one proximal annular member, at least one distal annular member and at least one medial annular member, each of said annular members having a radially compact configuration and a radially expanded configuration;

at least first and second strut members each connected to and extending between said proximal and medial annular members, each said strut members having a pre-expansion configuration and a post-expansion configuration, wherein the post-expansion configuration of said at least one first strut member is curved in a first direction and the post-expansion configuration of said at least one second strut member is curved in a second direction, such that said first and second strut members combine to provide a serpentine configuration so as to maintain a patent serpentine fluid flow path between the first and second conduits and through the device;

said device being initially transluminally deliverable with its annular members in their radially collapsed configurations and said first and second strut members in their pre-expansion configurations; and, said device being thereafter implantable with its annular members in their radially expanded configurations and its first and second strut members in their post-expansion configurations.

30. The device of claim 29 wherein said at least one first and second strut members comprise a plurality of first and second strut members.

31. The device of claim 30 having 4 to 8 first strut members and 4–8 second strut members.

32. The device of claim 29 wherein adjacent ones of said first and second strut members are spaced apart from each other and disposed about a central axis when the device is implanted, such that a hollow channel is defined within said strut members.

33. The device of claim 29 wherein said first and second strut members are formed of resilient material such that they remain in their pre-expansion configurations when radially constrained, but will assume their post-expansion configurations when radially unconstrained.

34. The device of claim 33 wherein said resilient material is selected from the group of resilient materials consisting of:
spring metal;
a resilient polymer; and,
a shape memory alloy.

35. The device of claim 29 wherein said first and second strut members are formed of malleable material.

36. The device of claim 35 wherein said malleable material is selected from the group of malleable materials consisting of:
plastically deformable metal; and,
plastically deformable polymer.

37. The device of claim 29 wherein at least some of said proximal, distal and medial annular members are of different size when in their radially expanded configurations.

38. A system comprising:

a device for facilitating fluid flow between the lumen of a first anatomical conduit which has a first opening formed therein, and the lumen of a second anatomical conduit which has a second opening formed therein, said device comprising:

at least one proximal annular member, at least one distal annular member and at least one medial annular member, each of said annular members having a radially compact configuration and a radially expanded configuration;

at least one first strut member connected to and extending between said proximal and medial annular members, said at least one first strut member having a pre-expansion configuration and a post-expansion configuration, wherein the post-expansion configuration of said first strut member is curvilinear;

at least one second strut member connected to and extending between said medial and distal annular members, said at least one second strut member having a pre-expansion configuration and a post-expansion configuration, wherein the post-expansion configuration of said second strut member is curvilinear, and wherein the first and second curvilinear post-expansion strut members are configured to maintain a patent curvilinear fluid flow path between the first and second conduits and through the device;

said device being initially transluminally deliverable with its annular members in their radially collapsed configurations and said first and second strut members in their pre-expansion configurations; and, said device being thereafter implantable with its annular members in their radially expanded configurations and its first and second strut members in their post-expansion configurations; and a pressure-exerting member positioned within said device and useable to cause the device to deform and become implanted such that its annular members are in their radially expanded configurations and its first and second strut members in their post-expansion configurations.

39. The system of claim 38 wherein said pressure-exerting device is a balloon which has a curved configuration when inflated to deform said first and second strut members to their curved post-expansion configurations.

40. The device of claim 29 wherein said annular members are self-expanding.

41. The device of claim 40 wherein said self-expanding annular members are formed of resilient material and are biased to their radially expanded configurations.

42. The device of claim 41 wherein said resilient material is selected from the group consisting of:
spring metal;
resilient polymer; and,
shape memory alloy.

43. The device of claim 29 wherein said annular members are pressure-expandable.

44. The device of claim 43 wherein said pressure-expandable annular members are formed of malleable material capable of being plastically deformed from their radially compact configurations to their radially expanded configurations.

45. The device of claim 44 wherein said malleable material is selected from the group of malleable materials consisting of:
plastically deformable metal; and
plastically deformable polymer.

46. The device of claim 29 wherein said first and second strut members have first and second ends, the first and second ends of said first strut members being fused to said proximal and medial annular members and the first and second ends of said second strut members being fused to said medial and distal annular members.

47. The device of claim 46 wherein said first and second strut members have first and second ends, the first and second ends of said first strut members are connected to said proximal and medial annular members by flexible connections and the first and second ends of said second strut members are connected to said medial and distal annular members by flexible connections.

48. The device of claim 47 wherein loops are formed on the first and second ends of said first and second strut members, and portions of said annular members are captured within said loops, to thereby form said flexible connections between the ends of said strut members and said annular members.

49. The device of claim 29 further comprising:
a plurality of transverse strut connector members formed between adjacent ones of said strut members.

50. A device for facilitating fluid flow between the lumen of a first anatomical conduit which has a first opening formed therein, and the lumen of a second anatomical conduit which has a second opening formed therein, said device comprising:
at least one proximal annular member, at least one distal annular member and at least one medial annular member, each of said annular members having a radially compact configuration and a radially expanded configuration;
at least first and second strut members each connected to and extending between said proximal and medial annular members, each said strut members having a pre-expansion configuration and a post-expansion configuration, wherein outer ones of said strut members have a longer radius of curvature than inner ones of said strut members when the device is implanted, and wherein said outer ones of said strut members are longer in length than said inner ones of said strut members, said outer ones of said strut members having at least one curvilinear wave formed therein while in their pre-expansion configurations so as to maintain a patent curvilinear fluid flow path between the first and second conduits and through the device;
said device being initially transluminally deliverable with its annular members in their radially collapsed configurations and said first and second strut members in their pre-expansion configurations; and,
said device being thereafter implantable with its annular members in their radially expanded configurations and its first and second strut members in their post-expansion configurations.

51. The device of claim 29 further comprising a pliable covering formed on at least a portion of said device.

52. The device of claim 51 wherein said pliable covering is a generally cylindrical covering formed about said device, said cover defining a hollow lumen which extends longitudinally through the device.

53. The device of claim 51 wherein at least one flow-through opening is formed in said pliable covering.

54. A device for facilitating fluid flow between the lumen of a first anatomical conduit which has a first opening formed therein, and the lumen of a second anatomical conduit which has a second opening formed therein, said device comprising:
at least one proximal annular member, at least one distal annular member and at least one medial annular member, each of said annular members having a radially compact configuration and a radially expanded configuration;
at least first and second strut members each connected to and extending between said proximal and medial annular members, each said strut members having a pre-expansion configuration and a post-expansion configuration, wherein the post-expansion configuration of each said strut members is curvilinear so as to maintain a patent curvilinear fluid flow path between the first and second conduits and through the device;
said device being initially transluminally deliverable with its annular members in their radially collapsed configurations and said first and second strut members in their pre-expansion configurations;
said device being thereafter implantable with its annular members in their radially expanded configurations and its first and second strut members in their post-expansion configurations; and
a pliable covering formed transversely across the device to block flow of body fluid.

55. The device of claim 29 wherein said first and second strut members combine to have a post-expansion configuration which is multicurvate, such that said proximal and distal annular members may be positioned at spaced-apart locations in the same anatomical conduit and said strut member may extend through said first and second openings and into a segment of an adjacent second anatomical conduit with said medial annular member being located within said second anatomical conduit.

56. A device for facilitating flow fluid between a first opening formed in an anatomical conduit and a second opening formed in an anatomical conduit, said device comprising:
at least one proximal annular member and at least one distal annular member, each of said annular members having a radially compact configuration and a radially expanded configuration;
at least one strut member connected to and extending between said proximal and distal annular members, said at least one strut member having a pre-expansion configuration and a post-expansion configuration, wherein outer ones of said strut members have a longer radius of curvature than inner ones of said strut members when the device is in its post-expansion configuration, and wherein said outer ones of said strut members are longer in length than said inner ones of said strut members, said outer ones of said strut members having at least one wave formed therein while the device is in its pre-expansion configuration;

said device being initially transluminally deliverable with its annular members in their radially collapsed configurations and said at least one strut member is in its pre-expansion configuration, wherein the proximal and distal annular members are coaxially positioned during transluminal delivery of the device; and, said device being thereafter implantable with its annular members are in their radially expanded configurations and said at least one strut member is in its post-expansion configuration.

57. A device for facilitating flow fluid between a first opening formed in an anatomical conduit and a second opening formed in an anatomical conduit, said device comprising:

at least one proximal annular member and at least one distal annular member, each of said annular members having a radially compact configuration and a radially expanded configuration;

at least one strut member connected to and extending between said proximal and distal annular members, said at least one strut member having a pre-expansion configuration and a post-expansion configuration;

said device being initially transluminally deliverable with its annular members in their radially collapsed configurations and said at least one strut member is in its pre-expansion configuration;

said device being thereafter implantable with its annular members are in their radially expanded configurations and said at least one strut member is in its post-expansion configuration; and, a pliable covering formed on at least a portion of said device, and formed transversely across the device to block flow of body fluid.

58. A device for facilitating fluid flow between the lumen of a first anatomical conduit which has a first opening formed therein, and the lumen of a second anatomical conduit which has a second opening formed therein, said device comprising:

at least one proximal annular member, at least one distal annular member and at least one medial annular member, each of said annular members having a radially compact configuration and a radially expanded configuration;

at least one first strut member connected to and extending between said proximal and medial annular members, said at least one first strut member having a pre-expansion configuration and a post-expansion configuration;

at least one second strut member connected to and extending between said medial and distal annular members, said at least one second strut member having a pre-expansion configuration and a post-expansion configuration, wherein the post-expansion configuration of said at least one first strut member is curved in a first direction and the post-expansion configuration of said at least one second strut member is curved in a second direction, such that said first and second strut members combine to provide a serpentine configuration;

said device being initially transluminally deliverable with its annular members in their radially collapsed configurations and said first and second strut members in their pre-expansion configurations; and, said device being thereafter implantable with its annular members in their radially expanded configurations and its first and second strut members in their post-expansion configurations.

59. A device for facilitating fluid flow between the lumen of a first anatomical conduit which has a first opening formed therein, and the lumen of a second anatomical conduit which has a second opening formed therein, said device comprising:

at least one proximal annular member, at least one distal annular member and at least one medial annular member, each of said annular members having a radially compact configuration and a radially expanded configuration;

at least one first strut member connected to and extending between said proximal and medial annular members, said at least one first strut member having a pre-expansion configuration and a post-expansion configuration;

at least one second strut member connected to and extending between said medial and distal annular members, said at least one second strut member having a pre-expansion configuration and a post-expansion configuration, wherein outer ones of said strut members have a longer radius of curvature than inner ones of said strut members when the device is implanted, and wherein said outer ones of said strut members are longer in length than said inner ones of said strut members, said outer ones of said strut members having at least one wave formed therein while in their pre-expansion configurations;

said device being initially transluminally deliverable with its annular members in their radially collapsed configurations and said first and second strut members in their pre-expansion configurations; and, said device being thereafter implantable with its annular members in their radially expanded configurations and its first and second strut members in their post-expansion configurations.

60. A device for facilitating fluid flow between the lumen of a first anatomical conduit which has a first opening formed therein, and the lumen of a second anatomical conduit which has a second opening formed therein, said device comprising:

at least one proximal annular member, at least one distal annular member and at least one medial annular member, each of said annular members having a radially compact configuration and a radially expanded configuration;

at least one first strut member connected to and extending between said proximal and medial annular members, said at least one first strut member having a pre-expansion configuration and a post-expansion configuration;

at least one second strut member connected to and extending between said medial and distal annular members, said at least one second strut member having a pre-expansion configuration and a post-expansion configuration;

said device being initially transluminally deliverable with its annular members in their radially collapsed configurations and said first and second strut members in their pre-expansion configurations;

said device being thereafter implantable with its annular members in their radially expanded configurations and its first and second strut members in their post-expansion configurations; and, a pliable covering formed on at least a portion of said device, and formed transversely across the device to block flow of body fluid.

61. The device of claim 26 wherein said at least one strut member comprises a plurality of strut members.

62. The device of claim 26 having 4 to 8 strut members.

63. The device of claim 26 wherein said strut members are spaced apart from each other and disposed about a central axis when the device is in its implanted state, such that a hollow channel is defined within said strut members.

64. The device of claim 26 wherein said at least one strut member is formed of resilient material such that it remains in its pre-expansion configuration when radially constrained, but will assume its post-expansion configuration when radially unconstrained.

65. The device of claim 64 wherein said resilient material is selected from the group of resilient materials consisting of:
   spring metal;
   a resilient polymer; and,
   a shape memory alloy.

66. The device of claim 26 wherein said at least one strut member(s) is/are formed of malleable material.

67. The device of claim 66 wherein said malleable material is selected from the group of malleable materials consisting of:
   plastically deformable metal; and
   plastically deformable polymer.

68. The device of claim 26 wherein said annular members are self-expanding.

69. The device of claim 68 wherein said self-expanding annular members are formed of resilient material and are biased to their radially expanded configurations.

70. The device of claim 69 wherein said resilient material is selected from the group consisting of:
   spring metal;
   resilient polymer; and
   shape memory alloy.

71. The device of claim 26 wherein said annular members are pressure-expandable.

72. The device of claim 71 wherein said pressure-expandable annular members are formed of malleable material capable of being plastically deformed from their radially compact configurations to their radially expanded configurations.

73. The device of claim 72 wherein said malleable material is selected from the group of malleable materials consisting of:
   plastically deformable metal; and
   plastically deformable polymer.

74. The device of claim 26 wherein said at least one strut member has first and second ends, said first and second ends being fused to said first and distal annular members.

75. The device of claim 74 wherein said at least one strut member has first and second ends which are connected to said first and distal annular members by flexible connections.

76. The device of claim 74 wherein loops are formed on the first and second ends of said at least one strut member, and portions of said first and distal annular members are captured within said loops, to thereby form said flexible connections between the ends of said at least one strut member and first and distal annular members.

77. The device of claim 26 wherein the curvilinear post-expansion configuration of said at least one strut member is a serpentine configuration.

78. The device of claim 26 wherein the curvilinear post-expansion configuration of said at least one strut member is a generally U shaped configuration.

79. The device of claim 26 further comprising a plurality of transverse strut connector members formed between adjacent ones of said strut members.

80. The device of claim 26 wherein outer ones of said strut members have a longer radius of curvature than inner ones of said strut members when the device is in its second condition, and wherein said outer ones of said strut members are longer in length than said inner ones of said strut members, said outer ones of said strut members having at least one wave formed therein while the device is in its first condition.

81. The device of claim 26 wherein said pliable covering is a generally cylindrical covering formed about said device, said cover defining a hollow lumen which extends longitudinally through the device.

82. The device of claim 26 wherein at least one flow-through opening is formed in said pliable covering.

83. The device of claim 26 wherein said at least one strut member has a post-expansion configuration which is multicurvate, such that said proximal and distal annular members may be positioned at spaced-apart locations in the same anatomical conduit and said at least one strut member may extend through said first and second openings and through a segment of an adjacent second anatomical conduit.

84. The device of claim 59 wherein the proximal, distal and medial annular members are coaxially positioned during transluminal delivery of the device.

85. The device of claim 84 wherein the proximal and distal annular members have different longitudinal axes after the device has been implanted.

86. The device of claim 59 wherein said at least one first and second strut members comprise a plurality of first and second strut members.

87. The device of claim 86 having 4 to 8 first strut members and 4–8 second strut members.

88. The device of claim 86 wherein adjacent ones of said first and second strut members are spaced apart from each other and disposed about a central axis when the device is implanted, such that a hollow channel is defined within said strut members.

89. The device of claim 59 wherein said first and second strut members are formed of resilient material such that they remain in their pre-expansion configurations when radially constrained, but will assume their post-expansion configurations when radially unconstrained.

90. The device of claim 89 wherein said resilient material is selected from the group of resilient materials consisting of:
   spring metal;
   a resilient polymer; and
   a shape memory alloy.

91. The device of claim 59 wherein said first and second strut members are formed of malleable material.

92. The device of claim 91 wherein said malleable material is selected from the group of malleable materials consisting of:
   plastically deformable metal; and
   plastically deformable polymer.

93. The device of claim 59 wherein at least some of said proximal, distal and medial annular members are of different size when in their radially expanded configurations.

94. The device of claim 59 wherein said annular members are self-expanding.

95. The device of claim 59 wherein said self-expanding annular members are formed of resilient material and are biased to their radially expanded configurations.

96. The device of claim 95 wherein said resilient material is selected from the group consisting of:

spring metal;

resilient polymer; and shape memory alloy.

97. The device of claim 59 wherein said annular members are pressure-expandable.

98. The device of claim 97 wherein said pressure-expandable annular members are formed of malleable material capable of being plastically deformed from their radially compact configurations to their radially expanded configurations.

99. The device of claim 98 wherein said malleable material is selected from the group of malleable materials consisting of:

plastically deformable metal; and plastically deformable polymer.

100. The device of claim 59 wherein said first and second strut members have first and second ends, the first and second ends of said first strut members being fused to said proximal and medial annular members and the first and second ends of said second strut members being fused to said medial and distal annular members.

101. The device of claim 59 wherein said first and second strut members have first and second ends, the first and second ends of said first strut members are connected to said proximal and medial annular members by flexible connections and the first and second ends of said second strut members are connected to said medial and distal annular members by flexible connections.

102. The device of claim 101 wherein loops are formed on the first and second ends of said first and second strut members, and portions of said annular members are captured within said loops, to thereby form said flexible connections between the ends of said strut members and said annular members.

103. The device of claim 59 further comprising a plurality of transverse strut connector members formed between adjacent ones of said strut members.

104. The device of claim 60 wherein the proximal, distal and medial annular members are coaxially positioned during transluminal delivery of the device.

105. The device of claim 104 wherein the proximal and distal annular members have different longitudinal axes after the device has been implanted.

106. The device of claim 60 wherein said at least one first and second strut members comprise a plurality of first and second strut members.

107. The device of claim 106 having 4 to 8 first strut members and 4–8 second strut members.

108. The device of claim 106 wherein adjacent ones of said first and second strut members are spaced apart from each other and disposed about a central axis when the device is implanted, such that a hollow channel is defined within said strut members.

109. The device of claim 60 wherein said first and second strut members are formed of resilient material such that they remain in their pre-expansion configurations when radially constrained, but will assume their post-expansion configurations when radially unconstrained.

110. The device of claim 109 wherein said resilient material is selected from the group of resilient materials consisting of:

spring metal;

a resilient polymer; and a shape memory alloy.

111. The device of claim 60 wherein said first and second strut members are formed of malleable material.

112. The device of claim 111 wherein said malleable material is selected from the group of malleable materials consisting of:

plastically deformable metal; and plastically deformable polymer.

113. The device of claim 60 wherein at least some of said proximal, distal and medial annular members are of different size when in their radially expanded configurations.

114. The device of claim 60 wherein said annular members are self-expanding.

115. The device of claim 60 wherein said self-expanding annular members are formed of resilient material and are biased to their radially expanded configurations.

116. The device of claim 115 wherein said resilient material is selected from the group consisting of:

spring metal;

resilient polymer; and shape memory alloy.

117. The device of claim 60 wherein said annular members are pressure-expandable.

118. The device of claim 117 wherein said pressure-expandable annular members are formed of malleable material capable of being plastically deformed from their radially compact configurations to their radially expanded configurations.

119. The device of claim 118 wherein said malleable material is selected from the group of malleable materials consisting of:

plastically deformable metal; and plastically deformable polymer.

120. The device of claim 60 wherein said first and second strut members have first and second ends, the first and second ends of said first strut members being fused to said proximal and medial annular members and the first and second ends of said second strut members being fused to said medial and distal annular members.

121. The device of claim 60 wherein said first and second strut members have first and second ends, the first and second ends of said first strut members are connected to said proximal and medial annular members by flexible connections and the first and second ends of said second strut members are connected to said medial and distal annular members by flexible connections.

122. The device of claim 121 wherein loops are formed on the first and second ends of said first and second strut members, and portions of said annular members are captured within said loops, to thereby form said flexible connections between the ends of said strut members and said annular members.

123. The device of claim 60 further comprising a plurality of transverse strut connector members formed between adjacent ones of said strut members.

124. The device of claim 60 wherein said pliable covering is a generally cylindrical covering formed about said device, said cover defining a hollow lumen which extends longitudinally through the device.

125. The device of claim 60 wherein at least one flow-through opening is formed in said pliable covering.

* * * * *